US012778534B2

(12) United States Patent
Datta et al.

(10) Patent No.: US 12,778,534 B2
(45) Date of Patent: Nov. 3, 2026

(54) SYSTEM AND METHOD FOR IMAGE QUALITY PROTOCOL OPTIMIZER

(71) Applicant: GE Precision Healthcare LLC, Waukesha, WI (US)

(72) Inventors: Arka Datta, Täby (SE); John M. Boudry, Waukesha, WI (US); Clement Hemonnot, Waukesha, WI (US); Roy A. Nilsen, Waukesha, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 218 days.

(21) Appl. No.: 18/733,693

(22) Filed: Jun. 4, 2024

(65) Prior Publication Data

US 2025/0366812 A1 Dec. 4, 2025

(51) Int. Cl.
*A61B 6/00* (2024.01)
*A61B 6/46* (2024.01)
*A61B 6/58* (2024.01)

(52) U.S. Cl.
CPC .............. *A61B 6/545* (2013.01); *A61B 6/465* (2013.01); *A61B 6/467* (2013.01); *A61B 6/582* (2013.01)

(58) Field of Classification Search
CPC ......... A61B 6/545; A61B 6/582; A61B 6/032; A61B 6/4488; A61B 6/54; A61B 6/465; A61B 6/467
See application file for complete search history.

(56) References Cited

U.S. PATENT DOCUMENTS 7,233,645 B2 6/2007 Feda
7,313,216 B2 12/2007 Nishide et al.
8,503,615 B2 * 8/2013 Hockersmith ........... H05G 1/36 378/127
9,299,171 B2 * 3/2016 Bredno .................. A61B 6/032
11,147,528 B2 10/2021 Thibault et al.
2004/0008819 A1 * 1/2004 Drummond .......... A61B 6/0487 378/162
2016/0310763 A1 * 10/2016 Grady ...................... A61B 6/06
2021/0045706 A1 * 2/2021 Thibault ................. G21K 1/04
2021/0128820 A1 5/2021 Vaz et al.
2022/0061793 A1 3/2022 Vaz et al.
2023/0229925 A1 7/2023 Datta et al.
2025/0261922 A1 * 8/2025 Leussler .............. G01R 33/543

FOREIGN PATENT DOCUMENTS

CN 110916696 A * 3/2020 ............ A61B 6/032

* cited by examiner

*Primary Examiner* — Uzma Alam
*Assistant Examiner* — Richard O Toohey
(74) *Attorney, Agent, or Firm* — McCoy Russell LLP

(57) ABSTRACT

Methods and systems are provided for adaptively configuring time delays between scans of a scan sequence performed using an imaging system, to maintain a temperature of components of an X-ray tube of the imaging system within a threshold temperature. A software tool is provided that allows a user to import, modify, and/or create scan sequence protocols (e.g., such as image quality (IQ) protocols) using a dedicated graphical user interface (GUI). The software tool parses the scan sequence protocols, using a thermal physics model of the X-ray tube to calculate a plurality of adaptive delays to be inserted between each scan of the scan sequence, such that all the components of the tube stay within predefined thermal limits for robust IQ or within a thermal range typical of a clinical site's thermal operating range. Each adaptive delay may be of a different length of time.

19 Claims, 11 Drawing Sheets

800

| Protocol Index (802) | kV (804) | mA (806) | Focal Spot (808) | Exposure Time (810) | Collimation (812) |
|---|---|---|---|---|---|
| $P_1$ | $KV_1$ | $mA_1$ | $FS_1$ | $t'_1$ | $C_1$ |
| $P_2$ | $KV_2$ | $mA_2$ | $FS_2$ | $t'_2$ | $C_2$ |
| $P_3$ | $KV_3$ | $mA_3$ | $FS_3$ | $t'_3$ | $C_3$ |
| $P_4$ | $KV_4$ | $mA_4$ | $FS_4$ | $t'_4$ | $C_4$ |
| .. | .. | .. | .. | .. | .. |
| $P_n$ | $KV_n$ | $mA_n$ | $FS_n$ | $t'_n$ | $C_n$ |

FIG. 8

900

901

902 904

| SCAN SEQUENCE | DURATION |
|---|---|
| Water 20 Small Bowtie | 10 seconds |
| Water 20 Large Bowtie | 10 seconds |
| Large Gammex Low mA | 5 seconds |
| Small Gammex High mA | 5 seconds |

FIG. 9

SYSTEM AND METHOD FOR IMAGE QUALITY PROTOCOL OPTIMIZER

TECHNICAL FIELD

Embodiments of the subject matter disclosed herein relate to computerized tomography (CT) imaging systems, and more specifically to thermal management of X-ray tubes of CT scanners.

BACKGROUND

In computed tomography (CT) imaging systems, an electron beam generated by a cathode is directed towards a target within an X-ray tube. A fan-shaped or cone-shaped beam of X-rays produced by electrons colliding with the target is directed towards a subject, such as a patient. After being attenuated by the object, the X-rays impinge upon an array of X-ray detectors, generating a CT image.

The components of a CT scanner undergo thermal stress each time a CT scan is performed. In various cases, such as during CT calibration, it is desired to perform multiple CT scans in sequence. Performing a sequence of CT scans often causes thermal stresses to accumulate in the components of the CT scanner. Existing techniques attempt to protect the components of the CT scanner from such accumulated thermal stress include inserting fixed or variable time delays between successive CT scans. However, the fixed or variable time delays may result in CT scan sequences that are excessively time-consuming.

SUMMARY

The current disclosure at least partially addresses one or more of the above identified issues by a method for an imaging system, the method comprising receiving a scan sequence protocol for a sequence of scans to be performed using the imaging system; modifying the scan sequence protocol to include a delay between each scan and a subsequent scan of the scan sequence to reduce a temperature of one or more components of an X-ray tube of the imaging system to a target temperature for performing the subsequent scan, where the delay has a duration that is customized to the scan and the subsequent scan; and executing the modified scan sequence using the imaging system.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIG. 8 is an exemplary lookup table, in accordance with one or more embodiments of the present disclosure;

FIG. 9 is an exemplary list of CT scans of an exemplary scan sequence, where the CT scans are ordered by duration, in accordance with one or more embodiments of the present disclosure;

Figure 1:
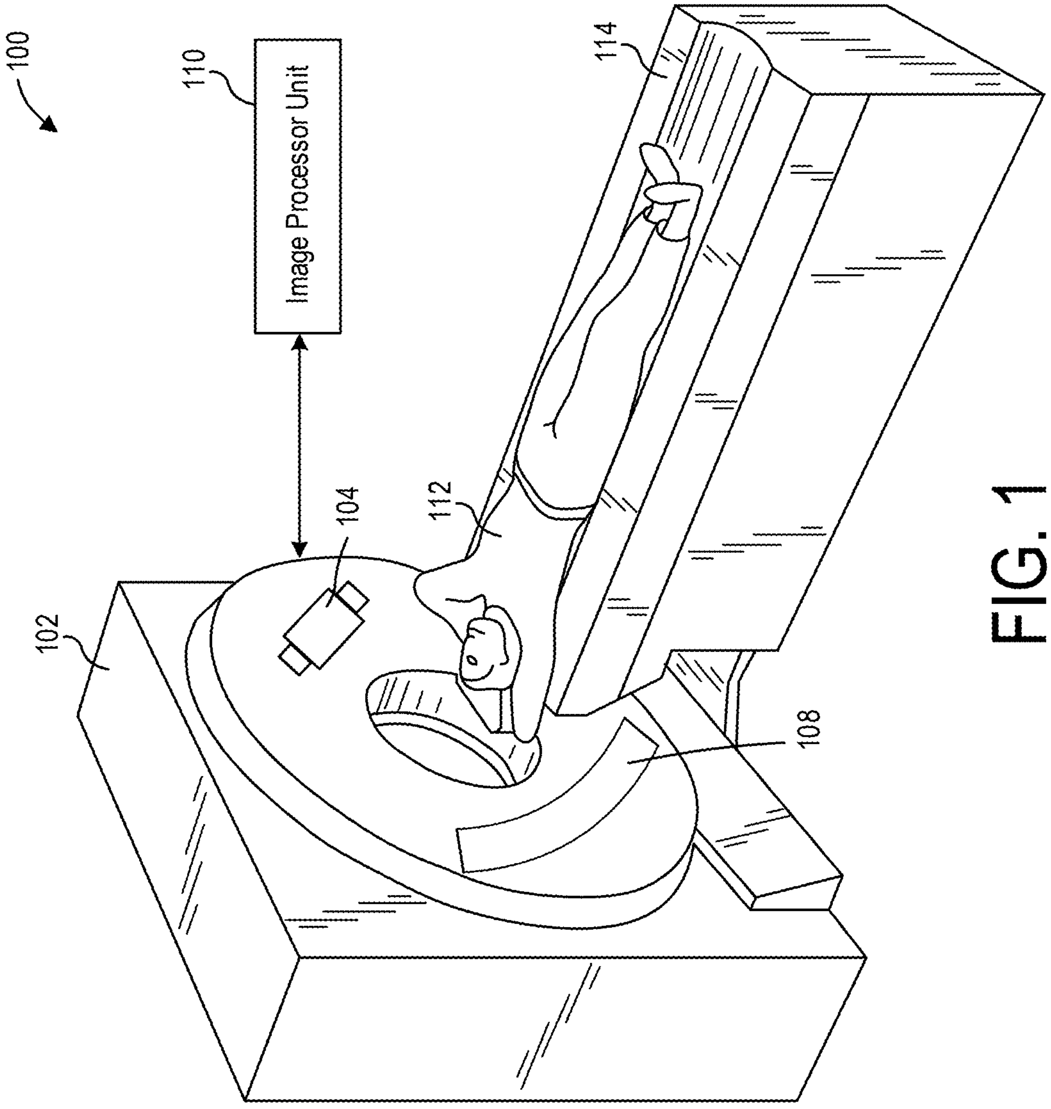
FIG. 1 shows a pictorial view of a computed tomography (CT) imaging system, in accordance with one or more embodiments of the present disclosure.

The drawings illustrate specific aspects of the described systems and methods. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

This description and embodiments of the subject matter disclosed herein relate to methods and systems for reducing an amount of time spent performing image quality (IQ) scans of a computed tomography (CT) system as part of a quality assurance (QA) procedure.

Typically, in computed tomography (CT) imaging systems, an X-ray source or X-ray tube emits a fan-shaped beam or a cone-shaped beam towards an object, such as a patient. The beam, after being attenuated by the patient, impinges upon an array of radiation detectors. An intensity of the attenuated X-ray beam radiation received at the detector array is typically dependent upon the attenuation of the X-ray beam by the patient. Each detector element of a detector array produces a separate electrical signal indicative of the attenuated beam received by each detector element. The electrical signals are transmitted to a data processing system for analysis. The data processing system processes the electrical signals to facilitate generation of an image.

Components of a CT scanner can experience thermal stress each time a CT scan is performed. In particular, the CT scanner can include one or more X-ray tubes, and such X-ray tubes can heat up (e.g., increase in temperature) each time a CT scan is implemented and/or otherwise executed.

In various cases, it can be desired to perform multiple CT scans in sequence. For example, calibration of a CT scanner may rely on the execution of a CT scan sequence (e.g., a sequential execution of a plurality of CT scans, one scan at a time) to ensure that the CT scanner is properly functioning, or to assess an image quality (IQ) performance of the CT scanner. As another example, a CT scanner that is serving multiple medical patients can be required to execute a CT scan sequence (e.g., one or more CT scans per patient, one patient at a time). An unfortunate side-effect of performing a sequence of CT scans can be an accumulation of thermal stresses in the components (e.g., X-ray tubes) of the CT scanner, which can potentially damage the CT scanner. Specifically, when multiple CT scans are sequentially performed by a CT scanner, heat can build up in the components of the CT scanner during each individual CT scan. Such heat can accumulate and/or compound throughout the sequential execution of the multiple CT scans, which can cause the components of the CT scanner to achieve very high temperatures.

Existing techniques attempt to protect the components of the CT scanner from accumulated thermal stresses include inserting fixed or variable time delays between successive CT scans. That is, when existing techniques are implemented, a first CT scan is performed which can cause the components of the CT scanner to heat up, then a first time delay is implemented which allows the components of the CT scanner to cool down (e.g., which allows the heat generated by the first CT scan to dissipate). A second CT scan is then performed which causes the components of the CT scanner to heat up again, and then a second time delay is implemented which allows the components of the CT scanner to cool down again (e.g., which allows the heat generated by the second CT scan to dissipate), and so on. These existing techniques may rely solely on time delay duration to protect the CT scanner from accumulation of thermal stresses and to protect the CT scanner from overheating. These delays may be in addition to other delays implemented to ensure that thermal limits of the components are not reached. Unfortunately, such existing techniques can result in CT scan sequences that are excessively time-consuming (e.g., may result in time delays that are longer than desired).

One approach to reducing the time spent performing a scan sequence with inter-scan time delays is to change an order in which CT scans of the sequence are performed. In some examples, a specific order in which CT scans of a sequence are performed can increase and/or decrease the accumulation of thermal stresses experienced by the CT scanner, in terms of a maximum measured temperature and/or average measured temperature. Thus, an analysis component may be used to identify or determine specific protocols including an order of CT scans that is predicted to reduce or control thermal stresses experienced by the CT scanner. However, this approach may not significantly reduce the times of CT scan sequences, whereby CT scan sequence times may still be undesirably long even after adjusting the order of the CT scans.

To address this issue, systems and methods are proposed herein to adaptively configure the time delays in CT scan sequences to intelligently control tube temperatures during CT scan sequences. A software tool is provided that allows a user to import, modify, and/or create scan sequence protocols (e.g., such as IQ protocols) using a dedicated graphical user interface (GUI). The software tool parses the scan sequence protocols, using a thermal physics model of the X-ray tube to calculate a plurality of adaptive delays to be inserted between each scan of the scan sequence, such that all the components of the tube stay within predefined thermal limits for robust IQ or within a thermal range typical of a clinical site's thermal operating range. Each adaptive delay may be of a different length of time. The scan sequence protocol may then be automatically updated with the new calculated adaptive delays, and the software tool calculates a total time estimate for performing the scan sequence that is displayed to the user via the GUI.

Additionally, the software tool may also provide options to the user for further reducing the total time for performing the scan sequence. For example, the user may specify a total amount of time to be allocated for a CT scan sequence, and the software tool may calculate delays that maximize an efficiency of usage of the total amount of time, and adjust a selected protocol accordingly. If not all of the CT scans of the scan sequence (including the delays) can be performed within the total amount of time, the software tool may determine a subset of CT scans to perform to best take advantage of the allocated time.

Thus, by using the software tool, protocols for CT scan sequences, such as regularly performed IQ and other calibration protocols, may be advantageously adjusted to reduce an amount of heat to which components of a CT imaging system are exposed and/or reduce an amount of time taken for performing the CT scan sequences. As a result, an efficiency of use of the CT imaging system may be increased, improving an overall functionality of the CT imaging system. In particular, a throughput of the CT imaging system (e.g., an amount of patients scanned using the CT imaging system) may be increased, and a downtime (e.g., a time during which the CT imaging system is not available for scanning patients) may be reduced.

Referring now to the figures, FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments, multiple X-ray sources and detectors may be employed to project a plurality of X-ray radiation beams for acquiring projection data at different energy levels corresponding to the patient. In some embodiments, the X-ray source 104 may enable dual-energy gemstone spectral imaging (GSI) by rapid peak kilovoltage (kVp) switching. In some embodiments, the X-ray detector employed may be a photon-counting detector that is capable of differentiating X-ray photons of different energies.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an X-ray source projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of an X-ray radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging plane and around the object to be imaged such that an angle at which the X-ray beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector.

Figure 2:
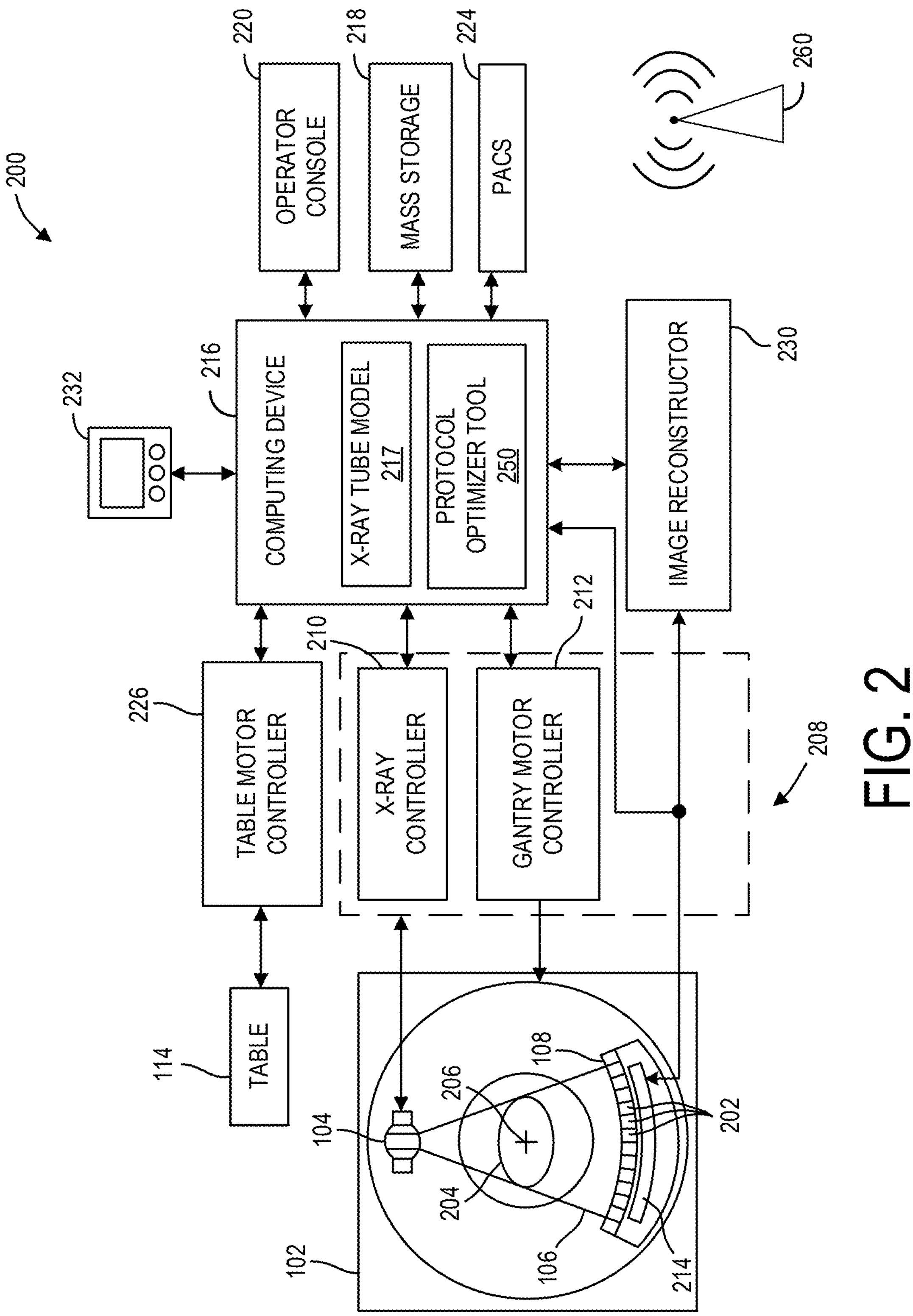
FIG. 2 shows a block schematic diagram of an example CT imaging system, in accordance with one or more embodiments of the present disclosure.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the X-ray radiation beam 106 (see FIG. 2) that pass through the subject 204 (such as a patient) to acquire corresponding projection data. In some embodiments, the detector array 108 may be fabricated in a multislice configuration including the plurality of rows of cells or detector elements 202, where one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector elements 202 of the detector array 108 may include photon-counting detectors which register the interactions of individual photons into one or more energy bins.

The acquired sets of projection data may be used for basis material decomposition (BMD). During BMD, the measured projections are converted to a set of material-density projections by applying MD calibration vectors. The material-density projections may be reconstructed to form a pair or a set of material-density maps or images of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Computing device 216 may include various AI models, which may be used, for example, to determine or adjust parameters of the imaging system 200, process and/or analyze results of a CT scan, and/or various perform various other processing tasks. In particular, the AI models may include an X-ray tube model 217, which may be a physics-based model used to simulate properties of an X-ray tube of imaging system 200 (e.g., X-ray source 104). For example, the X-ray tube model 217 may take as input a protocol for performing a hypothetical CT scan using imaging system 200, and the X-ray tube model 217 may output simulated properties of the X-ray tube as a consequence of performing the hypothetical CT scan. In particular, the X-ray tube model 217 may simulate a predicted temperature of various components of the X-ray tube. The X-ray tube model 217 may be used to determine suitable delays between acquisitions using the imaging system 200, as described in greater detail below. The X-ray tube model 217 may be created and/or trained based on historical and/or statistical data collected from the imaging system 200 using various techniques known in the art.

In particular, the X-ray tube model 217 may be used by a protocol optimizer software tool 250, which may be installed on computing device 216. Alternatively, the protocol optimizer software tool 250 may be installed on a different computing device external to X-ray imaging system 200, where the different computing device may be coupled to X-ray imaging system 200 via a wired or wireless network 260. For example, the different computing device may be a personal computing device of a radiologist, or a medical physicist that works with X-ray imaging system 200. The protocol optimizer software tool 250 may be used to modify a sequence of scans performed using X-ray imaging system 200, for example, to achieve image quality targets for images reconstructed from the scans included in the scan sequence. For example, during a calibration of the X-ray imaging system 200, an image quality test may be performed that relies on a sequence of CT scans meeting image quality goals. The modification of scan sequences using the protocol optimizer software tool 250 is described in greater detail below in reference to FIGS. 4-11.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a “cloud” network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Figure 3:
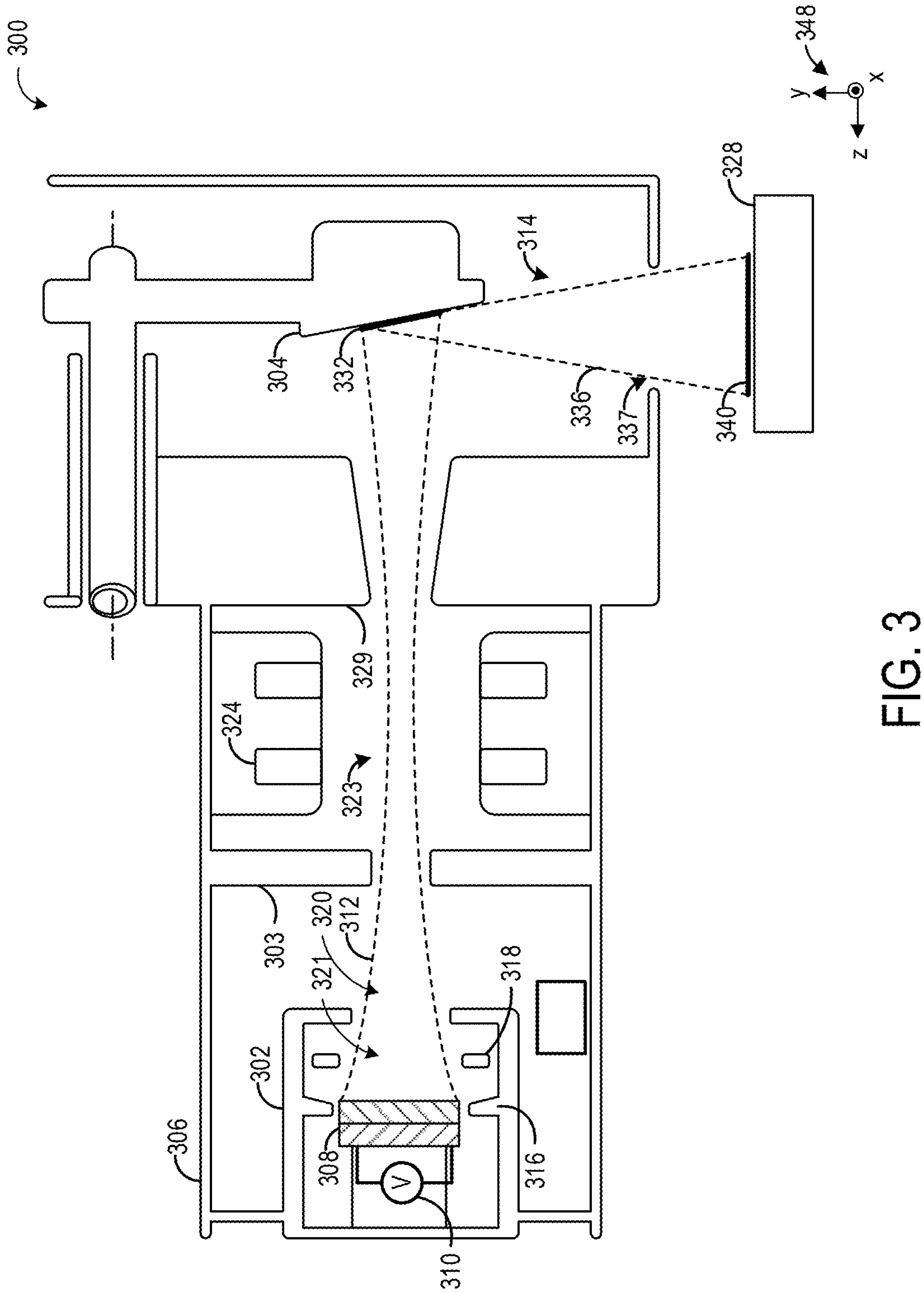
FIG. 3 is a schematic diagram of an exemplary X-ray tube, in accordance with one or more embodiments of the present disclosure.

Referring now to FIG. 3, an exemplary X-ray tube 300 of an X-ray system is shown. In one embodiment, the X-ray tube 300 may be the X-ray source 104 of the X-ray systems 100 and 200 of FIGS. 1-2, respectively. In the illustrated embodiment, the X-ray tube 300 includes an exemplary cathode 302 and an anode 303 disposed within a tube casing 306. The cathode may include a filament 308. The cathode 302, and in particular the filament 308, may be directly heated by passing a current through the filament 308, which may be supplied by a voltage source 310. In one embodiment, a current of about 10 amps (A) may be passed through the filament 308. The filament 308 may emit an electron beam 312 as a result of being heated by the current supplied by the voltage source 310. As used herein, the term “electron beam” may be used to refer to a stream of electrons that have substantially similar velocities.

The electron beam 312 may be directed towards a target 304 to produce X-rays 314. More particularly, the electron beam 312 may be accelerated from the filament 308 towards the target 304 by applying a potential difference between the filament 308 and the anode 303. In one embodiment, a high-voltage in a range from about 40 kV to about 450 kV may be applied to set up the potential difference between the filament 308 and the anode 303, thereby generating one or more electric fields 320 in the X-ray tube 300. In one embodiment, a high-voltage differential of about 140 kV may be applied between the filament 308 and the anode 303 to accelerate the electrons in the electron beam 312 towards the target 304. As an example, the filament 308 may be at a potential of about −140 kV and the anode 303 and target 304 may be at ground potential or about zero volts.

The electron beam 312 may impinge on the target 304 at a focal spot 332. When the electron beam 312 impinges upon the target 304, heat may be generated in the target 304 at a location of the focal spot 332, which may be significant enough to melt the target 304. In various embodiments, a rotating target may be used to mitigate the problem of heat generation in the target 304. For example, the target 304 may be configured to rotate such that the focal spot 332 generated by the electron beam 312 striking the target 304 does not strike the target 304 consistently at the same location, so that the target 304 may not melt. In various embodiments, the target 304 may include materials such as, but not limited to, tungsten or molybdenum.

The heat generated in the target 304 may also be reduced by adjusting a size of a focal spot on the target 304, where a smaller focal spot may generate a greater amount of heat at a specific location. An electron collector 329, held at a same potential as the target 304, serves as a sink of electrons that bounce off the surface of 304 during the initial impact, which reduces the chance of those same electrons re-striking the target. Collecting the backscattered electrons in this way further may reduce target heating. Nevertheless, heat may build up within X-ray tube 300 during operation of the X-ray tube 300. The heat may especially increase during sequences of scans using X-ray tube 300. As described in greater detail below, the heat may be reduced by including delays between individual scans included in the sequences.

The X-ray tube 300 may include one or more focusing electrodes 316, which may be disposed adjacent to the filament 308 such that the one or more focusing electrodes 316 focus the electron beam 312 towards the target 304. As used herein, the term "adjacent" means near to in space or position. To focus the electron beam 312, voltages may be applied to the one or more focusing electrodes 316 to generate the one or more electric fields 321. The voltages may be different for each of the one or more focusing electrodes 316.

Additionally, the X-ray tube 300 may include one or more extraction electrodes 318, which may be used for additionally controlling and focusing the electron beam 312 towards the anode 303. The one or more extraction electrodes 318 may be located between the anode 303 and the filament 308. In some embodiments, the one or more extraction electrodes 318 may be positively biased by supplying a desired voltage to the one or more extraction electrodes 318.

An energy of the electron beam 312 may be controlled in various ways. For instance, the energy the electron beam 312 may be controlled by altering the potential difference (e.g., an acceleration voltage) between the cathode 302 and the anode 303. As used herein, the term "electron beam current" refers to a flow of electrons per second between the cathode 302 and the anode 303. The current of the electron beam 312 may be controlled by adjusting the filament voltage to change the temperature of the filament 308. The electron beam current may be controlled by altering the voltage applied to the one or more extraction electrodes 318. It may be noted that the filament 308 may be treated as an infinite source of electrons.

The one or more electric fields 321 may be generated between the one or more extraction electrodes 318 and the one or more focusing electrodes 316 due to a potential difference between the one or more focusing electrodes 316 and the one or more extraction electrodes 318. A strength of the one or more electric fields 320 may be employed to control the intensity of electron beam 312 generated by the filament 308 towards the anode 303. More particularly, the one or more electric fields 320 may cause the electrons emitted by the filament 308 to be accelerated towards the anode 303. The stronger the one or more electric fields 320, the stronger the acceleration of the electrons from the filament 308 towards the anode 303. Alternatively, the weaker the one or more electric fields 320, the lesser the acceleration of electrons from the filament 308 towards the anode 303. The intensity of the electron beam 312 striking the target 304 may thus be controlled by the one or more electric fields 320 and 321.

Additionally, the X-ray tube 300 may also include one or more magnets 324 for focusing and/or positioning and deflecting the electron beam 312 onto the target 304. In various embodiments, the one or more magnets 324 may be disposed between the cathode 302 and the target 304. In some embodiments, the one or more magnets 324 may include one or more multipole magnets for influencing focusing of the electron beam 312 by creating one or more magnetic fields 323 that shapes the electron beam 312 on the target 304. The one or more multipole magnets may include one or more quadrupole magnets, one or more dipole magnets, or combinations thereof.

As properties of the electron beam current and voltage change, electrostatic focusing of the electron beam 312 will change accordingly. When the electron beam 312 has been focused and positioned, the electron beam 312 impinges upon the target 304 at a focal spot 332 to generate the X-rays 314. The X-rays 314 generated by collision of the electron beam 312 with the target 304 may be directed from the X-ray tube 300 through an opening in the tube casing 306, at an X-ray window 337, towards an object 328.

As a result of the electron beam 312 colliding with target 304 at the focal spot 332, a set of X-rays 336 may be generated and directed out X-ray window 337 towards the object 328. The set of X-rays 336 may intersect with the object 328 at an effective focal spot 340. A configuration of X-ray tube 300 and the effective focal spot is indicated by a set of reference coordinate axes 348.

As mentioned above, under some circumstances, CT scans may be performed in sequences using imaging system 200 and/or X-ray tube 300. For example, diagnostic image quality (IQ) scans may be performed on CT scanners using phantoms, as part of a quality assurance program. Such CT scan sequences may include 80-100 or more CT scans, for example. During a CT scan sequence, heat generated during each CT scan of the CT scan sequence may accumulate, which may cause thermal stress and/or damage of components of X-ray tube 300, such as the target 304.

Additionally, diagnostic IQ scan sequences can subject tube components of X-ray tube 300 to higher temperatures than typically used in operation on patients, which can cause artifacts in the IQ scans. Because of this, protocols used for the IQ scans may be modified to include delays between scans, so that the components of X-ray tube 300 are maintained within thermal limits. CT scan protocols may already incorporate some delays based on thermal limitations; however, the delays are typically implemented based on thermal limitations to prevent component failure, and may not be sufficient to prevent the occurrence of artifacts. As a result, additional delays based on IQ thermal limitations may also be imposed. For example, an exemplary IQ thermal threshold may be 350 degrees centigrade, meaning that the artifacts may appear when tube temperatures exceed 350°. The additional delays based on the IQ thermal limitations are typically of a standard duration.

As mentioned above, one problem with inserting the standardized delays is that a total time taken to perform a CT scan sequence may be undesirably long, resulting in a decreased throughput and an increased downtime of the imaging system. To address this, a scan sequence optimization process is proposed to calculate customized delays for each CT scan of a CT scan sequence, where each customized delay may have a duration specific to one or more CT scans of the CT scan sequence, and a total amount of time taken to perform the CT scan sequence including the customized delays is less than a total amount of time taken to perform the CT scan sequence including the standardized delays.

Figure 4:
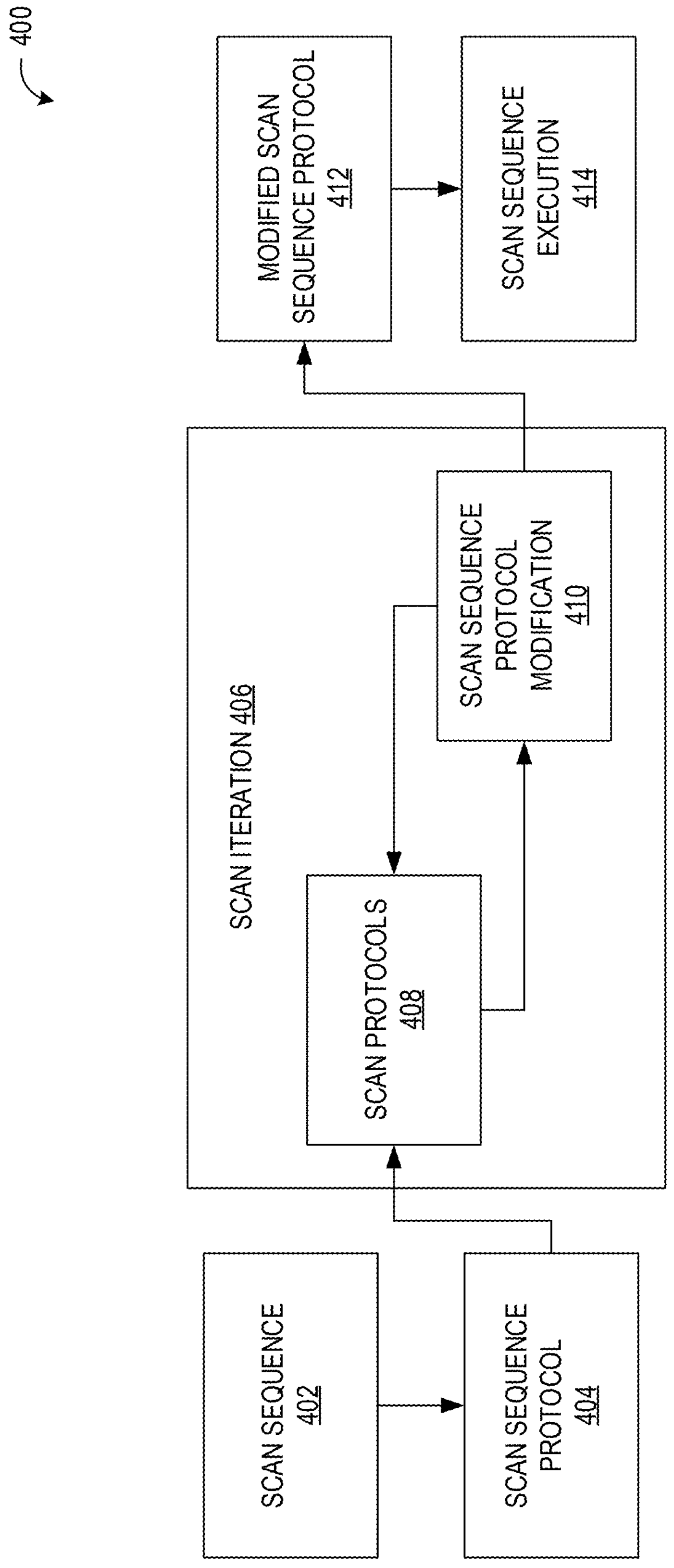
FIG. 4 is a schematic diagram of an exemplary workflow for modifying a sequence of CT scans, in accordance with one or more embodiments of the present disclosure.

FIG. 4 shows a high-level workflow 400 for reducing an amount of time spent performing a sequence of CT scans using an CT imaging system, such as CT imaging system 100 of FIG. 1 and/or imaging system 200 of FIG. 2, while maintaining the CT imaging system below an IQ thermal threshold, using scan sequence optimization based on customized delays.

In accordance with workflow 400, an operator of the CT imaging system may select a CT scan sequence 402 to be performed using the CT imaging system, where the CT scan sequence 402 includes include a plurality of CT scans that are performed sequentially. The CT scan sequence may be predefined and/or specified based on a selected clinical or calibration task. For example, an IQ calibration may be performed on the CT imaging system, and the IQ calibration may include a predefined set of CT scans. The CT scan sequence 402 may be defined by a scan sequence protocol 404, which may establish an order and a timing of the CT scans. In particular, the scan sequence protocol 404 may include delays of a standard, predefined length between performing each CT scan of the CT scan sequence 402, to maintain components of the CT imaging system below an IQ thermal threshold at which artifacts may occur in an image reconstructed using the CT imaging system. The standardized delays may extend a duration of the CT scan sequence 402.

To reduce the duration, for each CT scan, the scan sequence protocol may be modified at a scan sequence protocol modification block 410, to produce a modified scan sequence protocol 412. During the scan sequence protocol modification, the standardized delay included after the CT scan may be modified such that modified scan sequence protocol 412 includes an adjusted (e.g., customized) delay to be performed after the CT scan, and prior to a subsequent CT scan of the CT scan sequence.

To modify the scan sequence 402, in an iteration block 406, workflow 400 includes iterating over each CT scan of the scan sequence 402. For each CT scan in the sequence, a scan protocol 408 may be defined for performing each CT scan. The scan protocol 408 may include a plurality of scanning parameters and instructions for performing the desired CT scan. The defined protocol may be selected in advance by an operator of the CT imaging system, for example. The defined protocol may also be customized by the operator, in some examples.

At the scan sequence protocol modification block 410, a first scan protocol 408 of a current CT scan of the iteration and a second scan protocol 408 of a subsequent CT scan of the iteration may be analyzed to determine a suitable duration of a customized delay to be inserted between the current CT scan and the subsequent CT scan. The customized delay may be different from the standardized delay, and may be different between each CT scan of the CT scan sequence. Each customized delay included after a CT scan of the CT scan sequence may be calculated, during the scan sequence protocol modification block 410, to reduce a temperature of components (e.g., X-ray tube components) of the CT imaging system from a first predicted temperature achieved at an end of the current CT scan, to a second predicted temperature suitable for starting the subsequent CT scan, such that a predicted temperature of the components at an end of the subsequent CT scan will not exceed the thermal threshold. Once the modified scan sequence protocol 412 has been generated including the customized delays, the modified CT scan sequence protocol 412 may be executed at a scan sequence execution block 414 of workflow 400.

Figure 5:
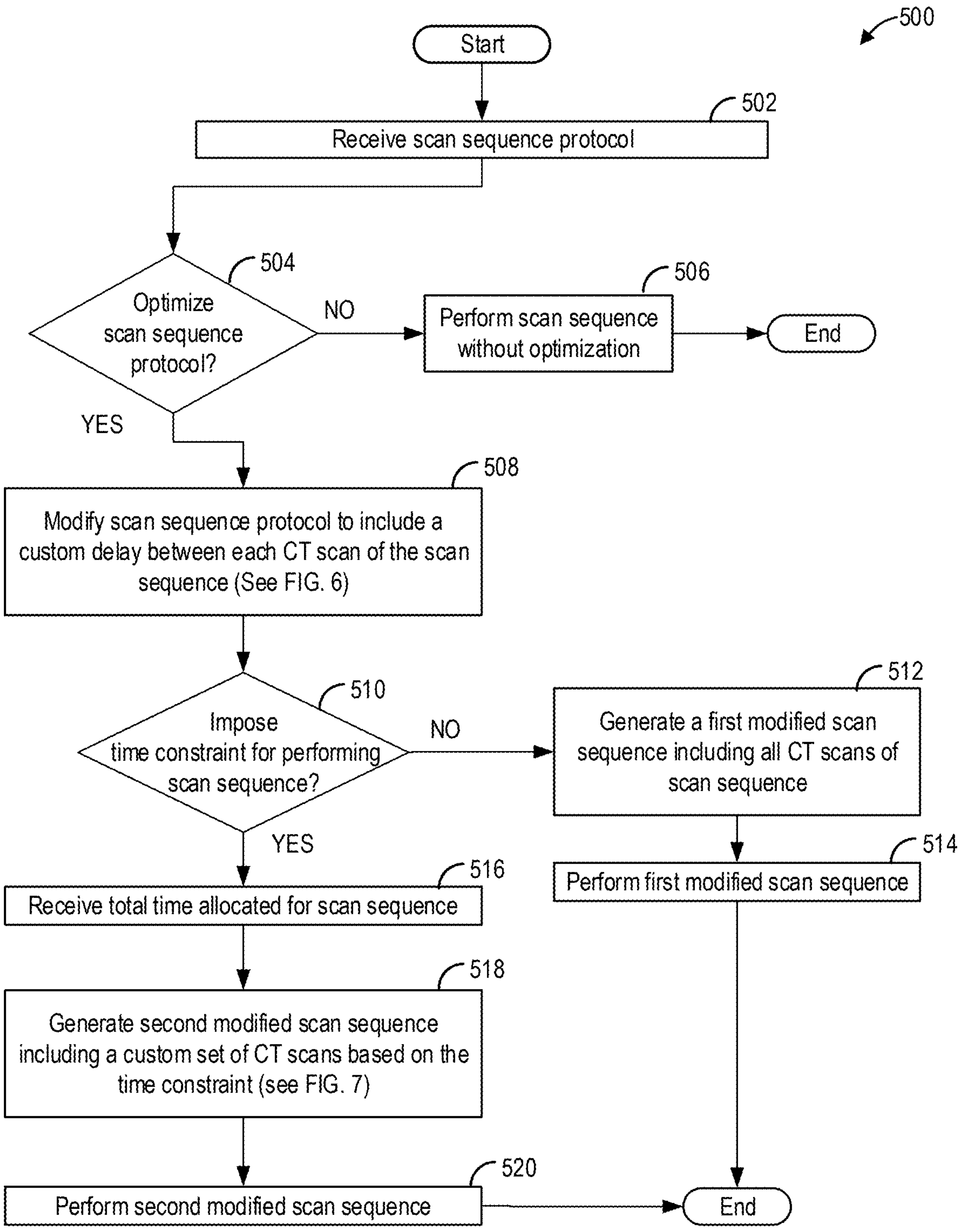
FIG. 5 is a flowchart illustrating a high-level method for modifying a sequence of CT scans to reduce a total duration of the sequence; in accordance with one or more embodiments of the present disclosure.

FIGS. 5 shows a high-level method 500 for implementing workflow 400 described above. Method 500 and other methods described herein may be executed by a processor of a CT imaging system, such as a processor of computing device 216 of imaging system 200 of FIG. 2, based on instructions stored in a memory of computing device 216. In particular, method 500 may be executed by a protocol optimizer software tool installed on computing device 216. In some embodiments, the protocol optimizer software tool may be installed on a different computing device, such as a computing device of an operator of the CT imaging system, where method 500 and the other methods described herein may be executed by a processor of the different computing device. The different computing device may be electronically coupled to the CT imaging system, in some examples.

Method 500 begins at 502, where method 500 includes receiving a scan sequence protocol of a sequence of CT scans to perform on the CT imaging system. The scan sequence protocol may be a non-limiting example of scan sequence protocol 404 of FIG. 4.

At 504, method 500 includes determining whether to optimize the scan sequence protocol by modifying the protocol to adjust delays inserted between each CT scan of the scan sequence. That is, an optimized scan sequence protocol may include, for each CT scan in the CT scan sequence, a custom delay that may be different from a standardized delay included in the scan sequence protocol for the respective CT scan. In various embodiments, the user may indicate whether to optimize the scan sequence protocol via one or more controls of the GUI. In some embodiments, the scan sequence protocol may be optimized by the protocol optimizer software tool as a default option, even if no input is provided by the user.

If at 504 it is determined that no indication has been provided or specified for optimizing the scan sequence protocol, method 500 proceeds to 506. At 506, method 500 includes performing the scan sequence in accordance with the scan sequence protocol without any modifications, and method 500 ends.

Alternatively, if at 504 it is determined that an indication has been provided or specified for optimizing the scan sequence protocol, method 500 proceeds to 508. At 508, method 500 includes optimizing the scan sequence protocol by calculating a custom delay to be inserted between each CT scan of the scan sequence, and modifying the scan sequence protocol to include the custom delay. Generating the custom delays is described in greater detail below in reference to FIG. 6.

At 510, method 500 includes determining whether to optimize the scan sequence protocol based on a time constraint, where the time constraint is a total amount of time allocated for the CT scan sequence (e.g., within which the CT scan sequence should be performed). In some embodiments, the time constraint may be inputted or selected by the user via the GUI. For example, the time constraint may be 16 hours, corresponding to two eight-hour shifts of operation. In other embodiments, the time constraint may be established as a default setting, or predefined based on a historical usage of the CT imaging system, for example. For example, a specific amount of time may be allocated for calibrating the CT imaging system, where the calibration includes performing a sequence of CT scans.

If at 510 it is determined that a time constraint has not been provided or specified, method 500 proceeds to 512. At 512, method 500 includes generating a first modified scan sequence based on an optimized scan sequence protocol, where the first modified scan sequence includes all the CT scans of the scan sequence. Method 500 proceeds to 514, where method 500 includes performing the first modified scan sequence, and method 500 ends.

Alternatively, if at 510 it is determined that a time constraint has been provided or specified, method 500 proceeds to 516. At 516, method 500 includes receiving the total amount of time allocated for the scan sequence, and method 500 proceeds to 518.

At 518, method 500 includes generating a second modified scan sequence based on the total amount of time allocated for the scan sequence, where the second modified scan sequence includes a custom set of CT scans, which may include a smaller number of CT scans than the CT scan sequence. Generating the second modified scan sequence is described in greater detail below in reference to FIG. 7. Method 500 proceeds to 516, where method 500 includes performing the second modified scan sequence, and method 500 ends.

Thus, in the embodiment of method 500, three options are provided to the user: a first option not to optimize the scan sequence, where the scan sequence is performed without any modification of the scan sequence protocol; a second option, to optimize the scan sequence where the custom delays are inserted between the CT scans and all the CT scans are performed; and a third option, to optimize the scan sequence protocol such that the scan sequence is performed within a specified time period, where some CT scans of the scan sequence may not be performed, and custom delays are inserted between the performed CT scans.

Figure 6:
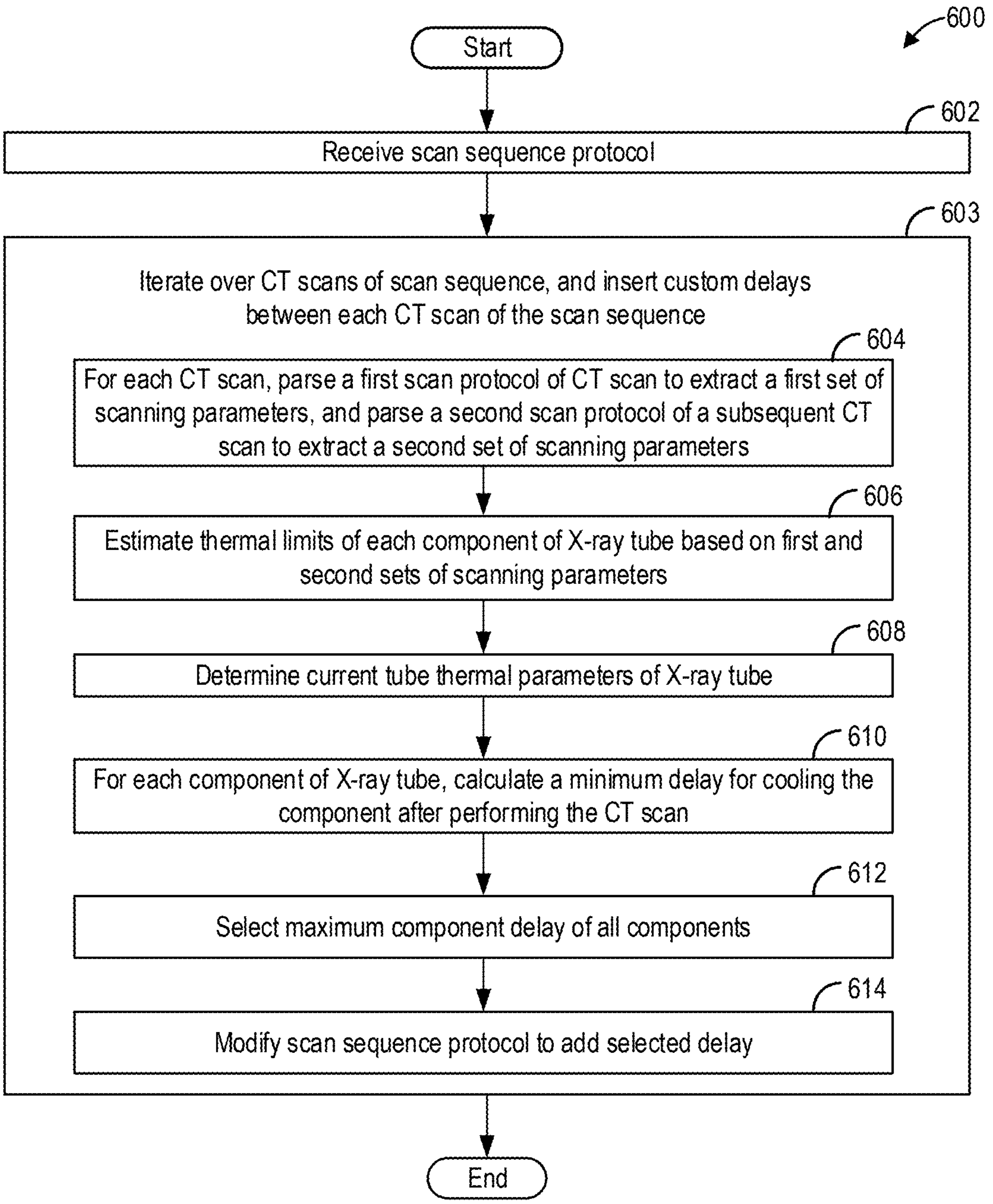
FIG. 6 is a flowchart illustrating a method for adjusting a sequence of CT scans to include a delay before performing a subsequent CT scan, in accordance with one or more embodiments of the present disclosure.

Referring now to FIG. 6, a detailed method 600 is shown for modifying a protocol of a CT scan sequence, to adjust a duration of a delay inserted between performing a CT scan of the scan sequence and performing a subsequent CT scan of the CT scan sequence. Thus, method 600 may be performed in an iterative fashion (e.g., during iteration block 406 of FIG. 4) for each CT scan of the CT scan sequence, where the CT scan sequence protocol is modified during each iteration until adjusted, customized delays have been inserted between each CT scan of the CT scan sequence. Method 600 may be performed as part of method 500 of FIG. 5, described above.

Method 600 begins at 602, where method 600 includes receiving a scan sequence protocol to be optimized. The scan sequence protocol may be selected by an operator of the CT imaging system via a GUI of the protocol optimizer software tool, such as the exemplary protocol optimizer GUI described below in reference to FIG. 10.

At 603, method 600 includes iterating over the CT scans included in the scan sequence protocol, and inserting custom delays between each CT scan of the scan sequence protocol.

At 604, iterating over the CT scans and inserting the custom delays includes, for each CT scan of the scan sequence, parsing a first scan protocol of the CT scan to extract a first set of scanning parameters used for the CT scan, and parsing a second scan protocol of a subsequent CT scan to extract a second set of scanning parameters used for the subsequent CT scan. For example, the scanning parameters may include as kV, mA, rotation speed, focal spot size, aperture, etc. In some examples, a set of scanning parameters that impact a temperature of an X-ray tube of the CT imaging system may be stored in a lookup table, and the first and/or second sets of scanning parameters may be retrieved from the lookup table based on a scan protocol identifier.

Referring briefly to FIG. 8, an exemplary scanning parameter lookup table 800 is shown, from which a set of scanning parameters for a scan protocol may be retrieved. Scanning parameter lookup table 800 includes six columns, and a plurality of rows, where each row represents a different scan protocol. A first column 802 includes a reference protocol index of a respective scan protocol, which may be a number or encoding used to identify the scan protocol. A second column 804 includes a voltage scan parameter setting of the respective scan protocol, measured in kilovolts (kV). A third column 806 includes a tube current scan parameter setting of the respective scan protocol, measured in milliamperes (mA). A fourth column 808 includes a focal spot size scan parameter setting of the respective scan protocol, which may be one of a plurality of supported focal spot sizes. In one example, the supported focal spot sizes include an extra small focal spot size, a small focal spot size, a large focal spot size, and an extra-large focal spot size. A fifth column 810 includes an exposure time scan parameter setting of the respective scan protocol, measured in milliseconds (ms). A sixth column 812 includes a collimation scan parameter setting of the respective scan protocol. Thus, based on the protocol index, a row of the lookup table may be selected that includes appropriate scanning parameter settings for scanning a phantom or a patient in accordance with the selected scan protocol. It should be appreciated that the example scan setting parameters shown in FIG. 8 are for illustration and not limitation, and in other embodiments, different scan setting parameters and/or a different number of scan setting parameters may be included without departing from the scope of this disclosure.

Returning to FIG. 6, at 606, iterating over the CT scans and inserting the custom delays includes estimating thermal limits of each component of the X-ray tube for the respective CT scan, based on the extracted first and second sets of scanning parameters. In various embodiments, the thermal limits of each component may be estimated by a physics-based model of the X-ray tube (e.g., X-ray tube model 217 of FIG. 2), and stored in a lookup table in a similar manner as shown in FIG. 6. For example, the physics-based model may take as input a set of scanning parameters, and may output the thermal limits of each component, based on the set of scanning parameters. In some examples, the physics-based model may take as input both of the first and second sets of scanning parameters, and output the thermal limits of each component.

At 608, iterating over the CT scans and inserting the custom delays includes determining tube thermal parameters of the X-ray tube. The tube thermal parameters may include predicted initial temperatures and/or desired (e.g., target) baseline temperatures of various components of the X-ray tube prior to performing the CT scan, such as a target, an exit window, various high-voltage connections, cathode elements, etc. of the X-ray tube. The tube thermals may be determined from the physics-based model.

At 610, iterating over the CT scans and inserting the custom delays includes calculating, for each component of a plurality of selected components of the X-ray tube, a minimum delay to be imposed after the CT scan for allowing the component to cool before initiating the subsequent CT scan of the CT scan sequence. The selected components may include components sensitive to heat damage, meaning, components that desired to be maintained below a predefined threshold temperature to maintain stable ongoing operation of the imaging system. The minimum delay may be calculated as a minimum amount of time, during which no X-rays are generated by the X-ray tube, it takes to reduce a temperature of the component from a first predicted temperature after performing the CT scan and prior to performing the subsequent CT scan, to a target temperature for performing the subsequent CT scan, as defined by the tube thermal parameters. In various embodiments, this may include fitting an optimization technique, such as least square, to calculate the minimum delay for achieving a target temperature, using the physics-based model. For example, a target temperature for the subsequent scan may be specified, and the model may be iteratively applied for different scan delays until the target temperature is achieved.

At 612, iterating over the CT scans and inserting the custom delays includes selecting a longest (e.g., a maximum) delay of the minimum delays of each of the components of the X-ray tube. In other words, the maximum delay may be equivalent to the minimum delay corresponding to the component that takes longest to cool to the target temperature. That is, the maximum delay may be a sufficient amount of time for all of the selected components to achieve the target temperature.

At 614, iterating over the CT scans and inserting the custom delays includes modifying the scan sequence protocol to insert the selected (e.g., maximum) delay between the CT scan and the subsequent CT scan. After delays have been inserted between each CT scan of the CT scan sequence, method 600 ends.

Figure 7:
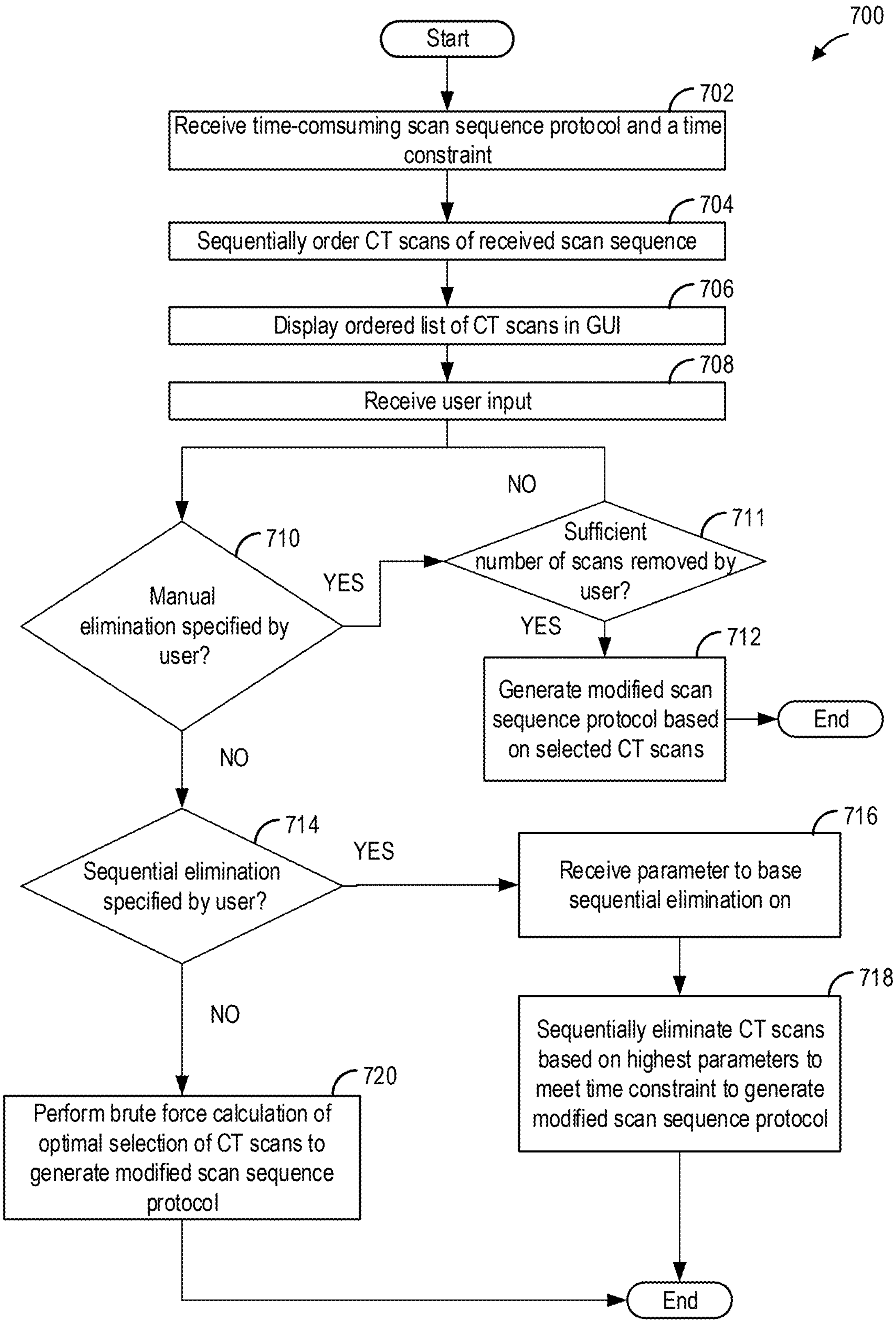
FIG. 7 is a flowchart illustrating a method for reducing a number of CT scans of a sequence of CT scans, in accordance with one or more embodiments of the present disclosure.

Referring now to FIG. 7, a detailed method 700 is shown for modifying a time-consuming CT scan sequence to be performed by a CT imaging system (e.g., CT imaging systems 100 and/or 200) within a specified amount of time, which may be less than an amount of time typically allocated to perform the time-consuming CT scan sequence. The time-consuming CT scan sequence may include a first number of CT scans, and a scan sequence protocol of the time-consuming CT scan sequence may be modified by method 700 to generate a modified CT scan sequence including a second, smaller number of CT scans. By eliminating one or more CT scans of the time-consuming CT scan sequence, an amount of time used to execute the modified CT scan sequence may be less than an amount of time used to execute the time-consuming CT scan sequence. As with methods 500 and 600, method 700 may be executed by an protocol optimizer software tool installed on a computing device, such as computing device 216 of FIG. 2.

Method 700 starts at 702, where method 700 includes receiving a time-consuming scan sequence protocol to be executed on the CT imaging system, and a time constraint for executing the time-consuming scan sequence based on the protocol. The time-consuming scan sequence may be a first modified scan sequence that has been previously modified to include a set of custom delays inserted between each CT scan of the scan sequence, for example, in accordance with method 600 of FIG. 6. Either or both of the time-consuming scan sequence and the time constraint may be inputted into the protocol optimizer software tool by a user via a GUI, such as the exemplary GUI described below in reference to FIG. 10.

At 704, method 700 includes generating a sequentially ordered list of the CT scans of the time-consuming scan sequence, based on a total duration of each CT scan, from a first CT scan that takes a longest amount of time, to a last CT scan of the time-consuming scan sequence that takes a shortest amount of time. The total duration of each CT scan may be extracted from a scan protocol of the CT scan and/or the time-consuming scan sequence protocol. The scan sequence protocol may include delays between each CT scan and a subsequent CT scan, such as the adjusted/custom delays generated via method 600. Thus, a duration of the time-consuming scan sequence may be a sum of the durations of each CT scan of the time-consuming scan sequence plus the durations of the delays included between each CT scan of the time-consuming scan sequence.

At 706, method 700 includes displaying the ordered list of CT scans on a display panel of the GUI to be reviewed by a user of the protocol optimizer software tool (e.g., an operator of the CT imaging system). When the ordered list is displayed, the ordered list may be reviewed by the user. A total duration of the time-consuming scan sequence may additionally be displayed in the GUI, along with a duration of each CT scan in the time-consuming scan sequence. In various examples, the user may be prompted to select between a plurality of options for reducing the total amount of time of the time-consuming scan sequence, and the protocol optimizer software tool may modify the time-consuming scan sequence based on input provided by the user via the GUI.

The plurality of options depicted in FIG. 7 includes three options. As a first option, the user may select to manually edit the ordered list of CT scans to reduce the total amount of time of the time-consuming scan sequence. Manually editing the ordered list may include removing one or more CT scans from the time-consuming scan sequence. Manually editing the ordered list may also include adjusting the order of one or more CT scans in the ordered list. When the user manually edits the ordered list to remove the one or more CT scans, the total amount of time of the scan sequence may be updated to reflect the removal of the one or more CT scans. The user may also add a removed CT scan back into the ordered list. For example, a removed CT scan may appear disabled (e.g., grayed out), and the user may select and re-enable the CT scan if desired.

Referring briefly to FIG. 9, an exemplary display panel 900 of the GUI shows a table 901 with an exemplary ordered list of CT scans comprising a scan sequence, as described above. A first column 902 of table 901 shows the ordered list of CT scans of the scan sequence (e.g., specified by a scan sequence protocol), and a second column 904 shows a duration of each CT scan. A total duration of the scan sequence is shown in a first row of table 901. Display panel 900 may be an interactive panel of the GUI, where elements of table 901 may be directly edited or reordered by a user of the GUI using an input device, such as a mouse. For example, the user may select CT scan 1, which has the longest duration of the CT scans, and remove it from the ordered list via standard UI controls (e.g., a delete button, a pop-up menu, etc.). When CT scan 1 is removed from the ordered list, the total duration of the scan sequence may be updated to reflect the removal of CT scan 1 (e.g., the duration of CT scan 1 may be subtracted from the total duration of the scan sequence). Additionally or alternatively, an order of the CT scans may be adjusted by the user, for example, by dragging and dropping a selected CT scan into a different position of the ordered list. Thus, using display panel 900, the user may iteratively remove CT scans until the total duration of the scan sequence is less than the time constraint. When the total duration is less than the time constraint, an indication of this may be displayed on display panel 900.

Returning to FIG. 7, as a second option, the user may select to have the scan sequence protocol automatically adjusted by the protocol optimizer software tool, where the protocol optimizer software tool may automatically remove one or more CT scans from the ordered list (e.g., without the one or more CT scans being selected by the user) by a process of sequential elimination based on a selected scan parameter. As a third option, the user may select to perform a brute force calculation of an optimal selection of one or more CT scans to be removed from the sequence. The first, second, and third options are described below in reference to specific steps of method 700.

At 708, method 700 includes receiving an input from the user with respect to a selected option of the three options. The input may be provided by the user via the GUI.

At 710, method 700 includes determining whether the user has selected the first option, for example to manually remove the one or more CT scans, using the display panel shown in FIG. 9. The user may manually remove successive CT scans until the updated duration of the scan sequence is less than the time constraint.

If at 710 it is determined that the user has selected to manually remove the one or more CT scans, method 700 proceeds to 711. At 711, method 700 includes determining whether a sufficient number of CT scans have been removed to meet the time constraint. If at 711 it is determined that the user has manually removed a sufficient number of CT scans to meet the time constraint (e.g., where the total duration of the scan sequence is less than the time constraint), method 700 proceeds to 712. At 712, method 700 includes generating a modified scan sequence protocol based on the CT scans selected by the user (e.g., the CT scans of the ordered list not removed by the user). The modified scan sequence protocol may be a version of the time-consuming scan sequence protocol without the removed CT scans.

Alternatively, if at 710 it is determined that the user has not selected to manually remove CT scans from the scan sequence, method 700 proceeds to 714. At 714, method 700 includes determining whether the user has selected the second option for the one or more CT scans to be automatically removed from the ordered list via sequential elimination.

If at 714 it is determined that the user has selected the second option for sequential elimination, method 700 proceeds to 716. At 716, method 700 includes receiving a scan parameter from the user on which the automatic removal will be based. In various embodiments, the scan parameter may be selected from a list of scan parameters displayed in the GUI. The scan parameters may include, for example, a tube current, a peak voltage, a focal spot size, etc.

At 718, method 700 includes sequentially eliminating CT scans of the time-consuming scan sequence that have a highest value of the selected scan parameter, until the time constraint is met. For example, if the selected scan parameter is the tube current, the protocol optimizer software tool may remove a first CT scan having a highest tube current from the time-consuming scan sequence. If the updated duration of the scan sequence represented by the updated ordered list is still greater than the time constraint, the protocol optimizer software tool may remove a second CT scan having a second-highest tube current from the updated scan sequence. If the updated duration of the updated scan sequence is still greater than the time constraint, the protocol optimizer software tool may remove a third CT scan having a third-highest tube current from the updated scan sequence, and so on, until the total duration of the updated scan sequence is less than the time constraint.

Alternatively, if the selected scan parameter is the focal spot size, the protocol optimizer software tool may remove a first CT scan having a largest focal spot size from the time-consuming scan sequence. If the updated duration of the scan sequence represented by the updated ordered list is still greater than the time constraint, the protocol optimizer software tool may remove a second CT scan having a second-largest focal spot size from the updated scan sequence, and so on, until the total duration of the updated scan sequence is less than the time constraint.

When the total duration of the updated scan sequence is less than the time constraint, the protocol optimizer software tool may generate a modified scan sequence protocol (modified scan sequence protocol 412) based on the CT scans included in the updated scan sequence (e.g., that are not removed). In other words, the modified scan sequence protocol may be a second modified scan sequence protocol, where the first modified scan sequence protocol is generated from an initial scan sequence protocol by following one or more steps of method 600 of FIG. 6, and the second modified scan sequence protocol is generated by removing a portion of the CT scans of the first modified scan sequence protocol by following one or more steps of method 700.

Returning to 714, if at 714 it is determined that the user has not selected the second option for sequential elimination of the CT scans, method 700 proceeds to 720. At 720, method 700 includes performing a brute force calculation of an optimal selection of CT scans to include in a modified scan sequence protocol, where the optimal selection of CT scans maximizes a number of CT scans performed in the modified scan sequence while maintaining the duration of the modified scan sequence below the time constraint. The brute force calculation may determine modified scan sequence durations for a range of combinations of the CT scans included in the time-consuming scan sequence, where each CT scan may have a range of combinations of scan parameter settings. The modified scan sequence durations may be stored, and a modified scan sequence protocol may be generated that includes a highest number of CT scans while maintaining the duration of the modified scan sequence below the time constraint.

Figure 10:
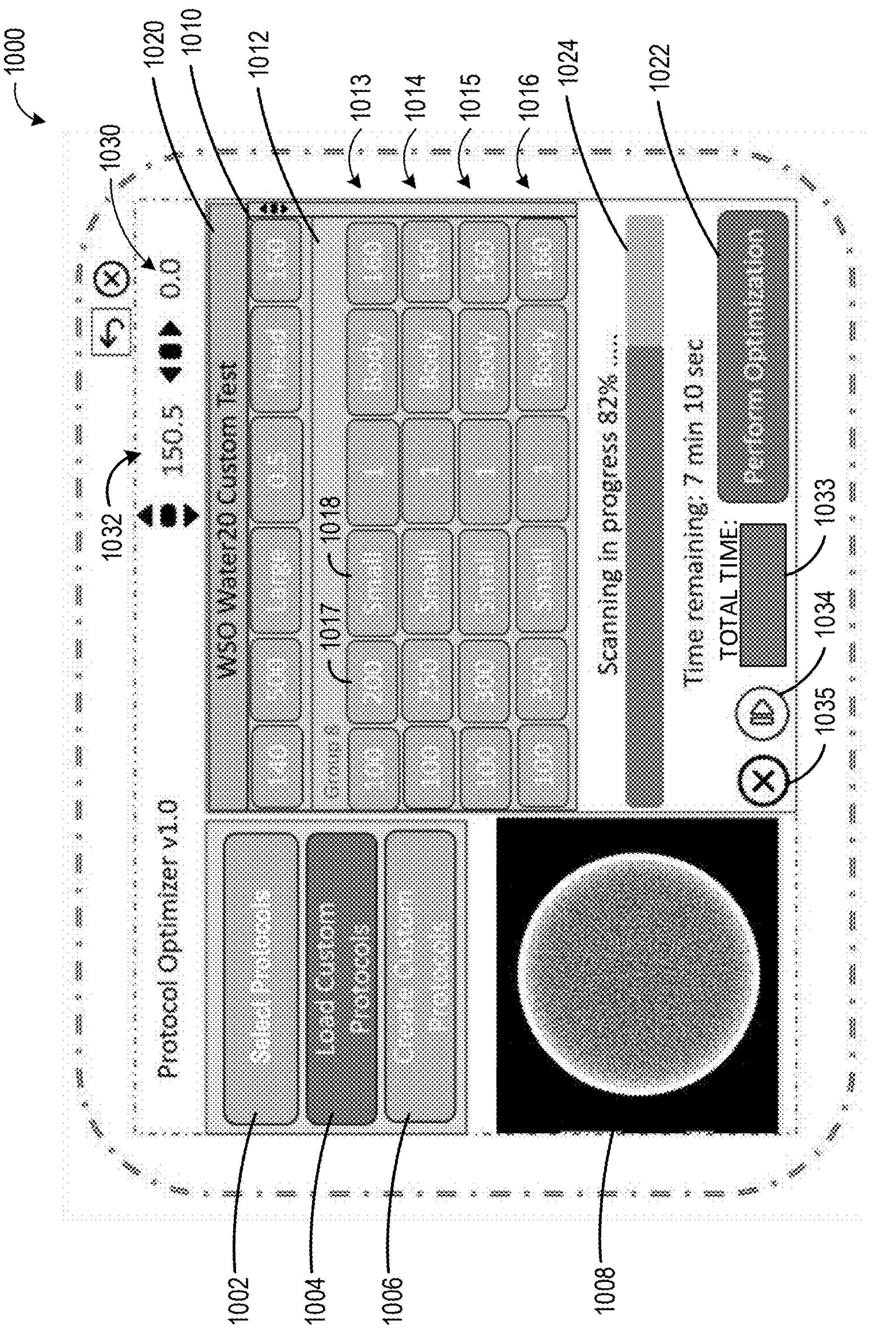
FIG. 10 is an exemplary GUI of a software tool for modifying a sequence of CT scans to reduce a total duration of the sequence, in accordance with one or more embodiments of the present disclosure.

FIG. 10 shows an exemplary GUI 1000 of the protocol optimizer software tool described herein (e.g., protocol optimizer software tool 250 of FIG. 2). GUI 1000 may be used by a user of the protocol optimizer software tool during the execution of methods 500, 600, and 700 described above. More specifically, GUI 1000 may be used to select, load, and/or create custom scan sequence protocols for a CT scan sequence, such as an IQ test sequence protocol, where the custom scan sequence protocols include custom delays of different durations that may be inserted between the CT scans of the CT scan sequence to ensure that a temperature of components of an X-ray tube (e.g., X-ray tube 300) are maintained below thermal limits. By using the custom scan sequence protocols, an overall amount of time taken to execute the CT scan sequence may be advantageously reduced, when compared with scan sequence protocols including standard delays of a same duration inserted between CT scans. Additionally, GUI 1000 may be used to further reduce the overall amount of time taken to execute the CT scan sequence, by selectively removing one or more CT scans from the CT scan sequence, as described above in reference to FIG. 7.

GUI 1000 may include a scan sequence protocol selection element 1002, a custom scan sequence protocol loading element 1004, and a custom scan sequence protocol creation element 1006. Scan sequence protocol selection element 1002 may be used to select a scan sequence protocol of a CT scan sequence, in order to modify the scan sequence protocol to include custom delays between each CT scan of the CT scan sequence, as described at step 508 of method 500. Custom scan sequence protocol loading element 1004 may be used to load a previously-created custom scan sequence protocol. Custom scan sequence protocol creation element 1006 may be used to create a new modified scan sequence protocol based on a selected and modified CT scan sequence.

A scan sequence protocol displayed in GUI 1000 may comprise a plurality of CT scan protocols, which may be grouped into various groups. When the user selects or loads a scan sequence protocol, scan parameter settings for each CT scan of the scan sequence may be displayed in a protocol display portion 1010 of GUI 1000. In the depicted example, four CT scan protocols included in a group 8 of the scan sequence are displayed: a first CT scan protocol 1013, a second CT scan protocol 1014, a third CT scan protocol 1015, and a fourth CT scan protocol 1016. Scan parameter settings included in each CT scan protocol are displayed horizontally in rows. For example, CT scan protocol 1013 includes a first parameter setting for peak voltage (KV) (e.g., 100); a second parameter setting for tube current (mA) (e.g., 200); a third parameter setting for focal spot size (e.g., small); a fourth parameter setting for exposure time (seconds) (e.g., 1); a fifth parameter setting for a bowtie filter used (e.g., Body); and a sixth parameter setting for collimation (e.g., 160). CT scan protocols 1014, 1015, and 1016 may be protocols that are grouped by peak voltage, where all the protocols in group 8 may share a same peak voltage.

Each scan parameter setting may be displayed in an interactive display element, such that the user may manually edit the scan parameter setting. For example, the user may edit the second parameter setting for tube current of first scan protocol 1013 (e.g., 200) by manually selecting and changing the parameter setting in a first interactive display element 1017; the user may edit the third parameter setting for focal spot size of first scan protocol 1013 (e.g., Small) by manually selecting and changing the parameter setting in a second interactive display element 1018; and so on. In this way, the user may include custom parameter settings in the scan protocols displayed in display portion 1010, if desired. Protocol display portion 1010 may also include a phantom identification bar 1020, which may describe a phantom on which the displayed scan sequence is performed. Additional information about the phantom may also be displayed in GUI 1000, such as a height 1032 of the phantom, an alignment 1030 of the phantom in a Z-dimension of a CT scanner, and/or different information.

When the scan sequence protocol displayed in GUI 1000 has been customized, the user may select a perform optimization button 1022 to optimize the scan sequence protocol. When the perform optimization button 1022 is selected, the protocol optimizer software tool may process the CT scan protocols in the scan sequence protocol (including modified CT scan protocols) to insert or adjust time delays between each CT scan of the CT scan sequence, in accordance with methods 500, 600, and 700 of FIGS. 5, 6, and 7, respectively. During the processing, the execution of the CT scans of the CT scan sequence may be simulated, and a progress of the simulation may be indicated via a progress bar 1024. A remaining time of the simulation/processing may also be displayed in GUI 1000.

As the execution of each CT scan is simulated, a resulting CT image reconstructed from the simulated data may be displayed in an image display panel 1008. Thus, the user may view a progression of the simulated reconstructed images of the CT scans as they are generated, to confirm that a desired or predicted IQ may be achieved using the customized scan sequence protocol. After the optimization has been performed, the user may select the custom scan sequence protocol creation element 1006 to store the custom scan sequence protocol in a memory of the protocol optimizer software tool. The custom scan sequence protocol may subsequently be exported to an imaging system (e.g., X-ray imaging system 200) to be performed, for example, as part of an IQ calibration of the imaging system.

GUI 1000 may also include a time constraint field 1033, in which the user may specify a total amount of time allocated for executing the displayed scan sequence. The optimization of the displayed scan sequence may be performed such that an execution time of the displayed scan sequence is maintained within the total amount of time allocated for executing the displayed scan sequence, in accordance with method 700.

For example, a radiologist may wish to run an IQ test scan sequence to calibrate a CT imaging system. However, an amount of time allocated for the IQ test scan sequence may be one day, and the IQ test scan sequence may take two days to complete, based on a scan sequence protocol of the IQ test scan sequence. As a result, the radiologist may wish to modify the scan sequence protocol, such that the modified IQ test scan sequence may be executed within the allocated time of one day.

To modify the scan sequence protocol, the radiologist may launch the protocol optimizer software tool. The protocol optimizer software tool may be launched on a computing device of the CT imaging system (e.g., computing device 216), or the protocol optimizer software tool may be launched on a computing device of the radiologist. An advantage of launching the protocol optimizer software tool the computing device of the radiologist is that computational and memory resources of the CT imaging system may not be relied on for performing the processing of the scan sequence protocol, where such resources may be advantageously used for performing CT scans on other patients, for example.

When the protocol optimizer software tool is launched, GUI 1000 may be displayed on a monitor screen of the computing device. Via the GUI 1000, the radiologist may select the scan sequence protocol selection element 1002, and a display panel may pop up with a list or menu of protocols to select from. The radiologist may select scan sequence protocol in the display panel. When the scan sequence protocol is selected, a plurality of individual CT scans included in the scan sequence and referenced by the scan sequence protocol may be displayed in protocol display portion 1010 of GUI 1000. Each CT scan of the plurality of individual CT scans may appear in a row of a scrollable list of CT scans, in some embodiments. For each CT scan, scanning parameters for performing the CT scan may be displayed along the row, in interactive display elements. The radiologist may adjust one or more scanning parameters of one or more CT scans of the plurality of individual CT scans.

A total amount of time of the scan sequence may be displayed in the GUI 1000, which may be greater than the allocated amount of time of one day. However, the total amount of time may include a plurality of standard delays included between each CT scan of the scan sequence, in accordance with the scan sequence protocol. To reduce the total amount of time, the radiologist may select the perform optimization button 1022 to insert custom delays between each CT scan of the scan sequence, where the custom delays may be of a shorter duration than the standardized delays. The protocol optimizer software tool may simulate performing each CT scan of the scan sequence to determine a suitable delay time to insert between the CT scans, and the radiologist may observe the progress of the protocol optimizer software tool and the updated total amount of time of the modified scan sequence including the custom delays.

However, after modifying the scan sequence, the updated total amount of time may still be greater than the allocated amount of time of one day. To modify the scan sequence protocol to shorten the scan sequence to meet the time constraint of one day, the radiologist may manually remove one or more CT scans of the plurality of individual CT scans, by selecting and removing a corresponding row. In some examples, a control element such as a forward arrow 1034 may be used to step through and select the rows/CT scans one by one, and a remove scan button 1035 may be selected to remove a selected row/CT scan. In this way, the radiologist may proceed to manually remove CT scans, until a displayed total amount of time of the scan sequence is less than the time constraint of one day. In some examples, the total time of the scan sequence may be displayed in GUI 1000, and the total time may be updated each time a CT scan is removed. In other examples, the radiologist may pop up an interactive display panel such as display panel 900 of FIG. 9, which may show a listing of the times of each CT scan of the scan sequence, and the radiologist may select and remove the CT scans using the interactive display panel.

As an alternative to manually removing CT scans as described above, the radiologist may perform an automatic optimization of the scan sequence by entering the time constraint (e.g., one day or 8 hours) into time constraint field 1033 and selecting the perform optimization button 1022. When the automatic optimization is selected, the protocol optimizer software tool may automatically determine which CT scans to remove from the scan sequence to generate a new, modified scan sequence protocol that can be performed within the time constraint.

When the radiologist enters in the time constraint and selects the perform optimization button, the radiologist may be prompted to select an option for modifying the scan sequence protocol, as described in reference to FIG. 7. As a first option, the radiologist may select to remove CT scans by sequential elimination. For this option, the radiologist may be prompted to select a scanning parameter, and the protocol optimizer software tool may rank or order the CT scans of the scan sequence in a descending order based on a magnitude of the scanning parameter. The protocol optimizer software tool may then remove CT scans in the descending order, in one embodiment. For example, the radiologist may select peak voltage, and the protocol optimizer software tool may remove a first CT scan having a highest peak voltage; a second CT scan having a second highest peak voltage; a third CT scan having a third highest peak voltage; and so on, until the total time of the scan sequence is less than the time constraint. In this way, CT scans may be sequentially eliminated until the sequence of CT scans may be performed within the allocated amount of time.

As a second option, the radiologist may select to perform the optimization of the scan sequence by calculating a total time of the scan sequence for all combinations of CT scans within the time constraint. When the radiologist selects the second option, the protocol optimizer software tool may selectively remove CT scans from the scan sequence to determine a plurality of sets of CT scans that may be performed within the time constraint. The protocol optimizer software tool may then select a set of CT scans that includes the greatest number of CT scans of the plurality of sets of CT scans. In other words, the protocol optimizer software tool may determine a scan sequence protocol that maximizes the number of CT scans included in the scan sequence protocol.

When a modified scan sequence protocol has been generated that meets the time constraint, the radiologist may select custom scan sequence protocol creation element 1006 to create and store the modified scan sequence protocol in a memory of the protocol optimizer software tool. After the modified scan sequence protocol has been stored, the radiologist may export the modified scan sequence protocol to the CT imaging system to perform the modified scan sequence during the scheduled calibration period. The radiologist may close the GUI 1000 to exit the protocol optimizer software tool.

Figure 11:
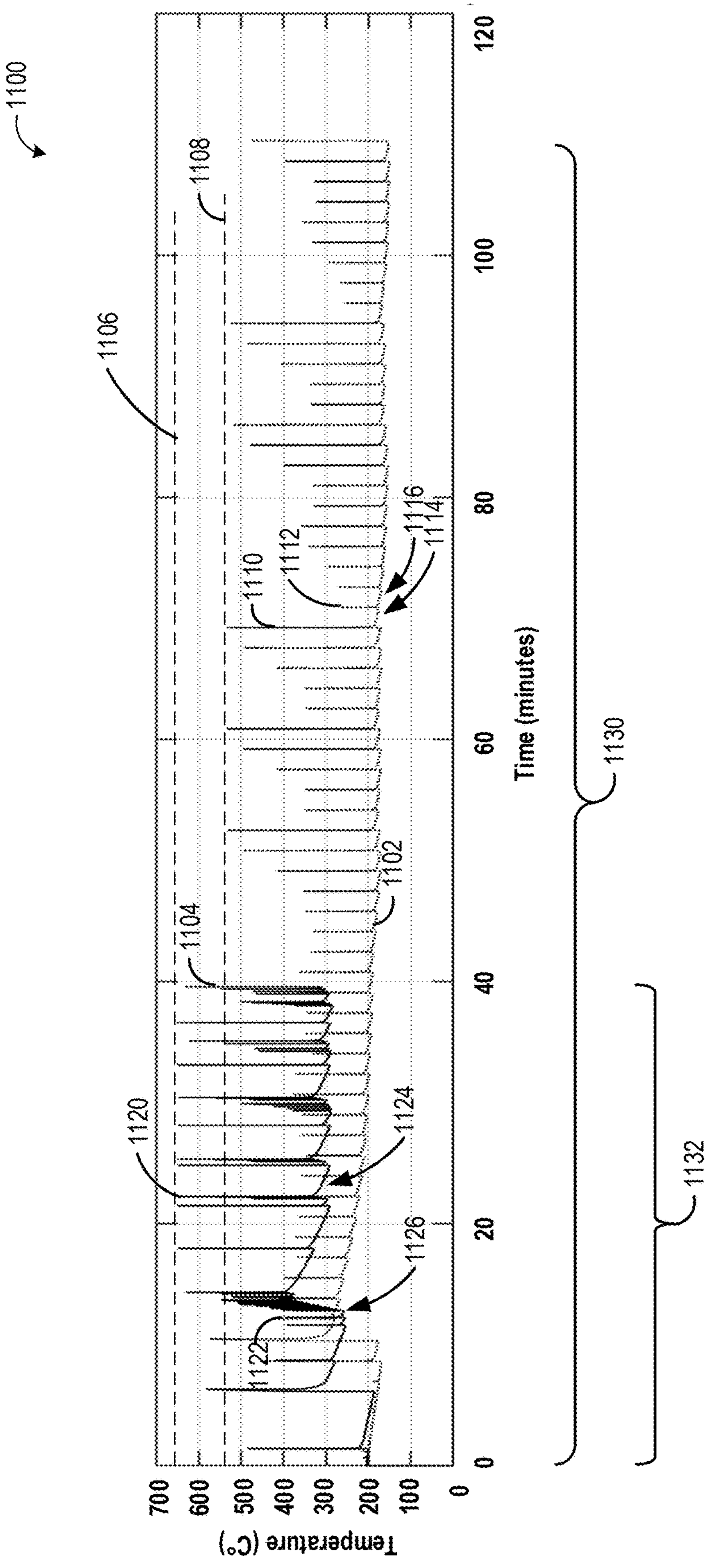
FIG. 11 is a graph showing a result of modifying a sequence of CT scans to reduce a total duration of the sequence, in accordance with one or more embodiments of the present disclosure.

Referring now to FIG. 11, a graph 1100 is shown depicting a result of applying methods 500, 600, and/or 700 to modify CT scan protocols of a sequence of CT scans to include custom delays inserted at the end of each CT scan and between consecutive CT scans of the CT scan sequence. Graph 11 includes two plots, a first plot 1102 and a second plot 1104, that indicate changes in a temperature of an exemplary X-ray tube component, shown on a vertical axis, over time, shown on a horizontal axis, while a sequence of CT scans is being performed. Each of the two plots 1102 and 1104 are characterized by a series of vertical or nearly vertical portions, representing increases (e.g., spikes) in temperature during performance of a CT scan of the CT scan sequence, that alternate with a series of horizontal or nearly horizontal portions representing delays between each CT scan of the CT scan sequence.

First plot 1102 shows a first implementation of the sequence of CT scans, in which delays of a standard length have been included between each CT scan of the sequence of CT scans to maintain the temperature of the exemplary X-ray tube component below a first temperature threshold 1108. For example, a first CT scan 1110 of plot 1102 generates a relatively large increase in temperature, from a starting temperature prior to executing first CT scan 1110 of approximately 200° C., to a highest temperature of approximately 550° C. at nearly the first temperature threshold 1108. A first standard delay 1114 is inserted after first CT scan 1110, during which the exemplary X-ray tube component cools back down to approximately 200° C., which may be a baseline temperature for initiating a second CT scan 1112. A second CT scan 1112 generates a smaller increase in temperature than first CT scan 1110, where at an end of second CT scan 1112, the temperature of the exemplary X-ray tube component is approximately 275° C. A second standard delay 1116 is inserted after second CT scan 1112, during which the exemplary X-ray tube component cools back down to approximately 200° C. Second standard delay 1116 and first standard delay 1114 have an equal duration, which is independent of a previous temperature increase. In other words, an equal amount of time is provided for the temperature of the exemplary X-ray tube component to decrease to the baseline temperature after first CT scan 1110 and second CT scan 1112, despite first CT scan 1110 generating a significantly higher increase in temperature. As a result of including the standard delays of equal duration after each CT scan in the CT scan sequence, a total amount of time 1130 taken to execute the CT scan sequence for first plot 1102 is approximately 110 minutes.

In contrast, second plot 1104 shows second implementation of the sequence of CT scans, in which delays of a different lengths have been included between each CT scan of the sequence of CT scans, in accordance with the methods described herein, to maintain the temperature of the exemplary X-ray tube component below a second temperature threshold 1106. For example, a third CT scan 1120 of plot 1102 generates a relatively large increase in temperature, from a starting temperature prior to executing first CT scan 1110 of approximately 300° C., to a highest temperature of approximately 650° C. at nearly the second temperature threshold 1106. A first custom delay 1124 is inserted after third CT scan 1120, during which the exemplary X-ray tube component cools back down to approximately 300° C. A fourth CT scan 1122 generates a smaller increase in temperature than third CT scan 1120, where at an end of fourth CT scan 1122, the temperature of the exemplary X-ray tube component is approximately 400° C. A second custom delay 1126 is inserted after fourth CT scan 1122, during which the exemplary X-ray tube component cools back down to approximately 275° C. Second custom delay 1126 and first custom delay 1124 have different durations, where the different durations are dependent on a previous temperature increase and a predicted subsequent temperature increase of a subsequent CT scan, in accordance with the methods provided herein. As a result of including the custom delays of different durations after each CT scan in the CT scan sequence, a total amount of time 1132 taken to execute the CT scan sequence for second plot 1104 is approximately 40 minutes.

Thus, when multiple CT scans are desired to be sequentially executed, using adaptive delays to intelligently control tube temperatures during a CT scan sequence, such as during an IQ scan, can help to reduce maximum and/or average internal temperatures of the CT scanner. Additionally, a total amount of time taken to execute the CT scan sequence can be advantageously reduced by incorporating the adaptive delays in the CT scan sequence protocol as described herein. In this way, the CT scanner can be protected from overheating without requiring unnecessarily long inter-scan time delays. The reduction in the total amount of time taken to execute the CT scan sequence may increase an availability of a CT imaging system, leading to an increased throughput (e.g., an increased number of CT scans and/or sequences that may be performed in a given day or shift) of the CT imaging system and increasing a general efficiency of the CT imaging system. Additionally, by using the adaptive delays rather than the delays of standard duration, X-ray tube components may be more precisely maintained within desired temperature ranges, resulting in increased useful lives of the X-ray tube components and a reduction in component failures.

Further, in situations where a CT scan sequence is desired to be performed, but an amount of time allocated for performing the CT scan sequence is less than a total amount of time the CT scan sequence takes to execute, the CT scan sequence can be shortened by using the software tool described herein. CT scans of the CT scan sequence may be selectively eliminated either via an efficient manual procedure, or automatically in accordance with a selected strategy. In an alternative situation where standard delays are inserted between the CT scans of the CT scan sequence, a much large number of CT scans would have to be eliminated for the CT scan sequence to be performed within the allocated time, and elimination of the CT scans would have to be performed manually in a time-consuming, laborious process.

The technical effect of including customized, adaptive delays between CT scans of a CT scan sequence rather than delays of a standard duration is that an overall amount of time taken to perform the CT scan sequence is reduced, thereby increasing a number of CT scans that can be performed by a CT scanner during an operational shift of the CT scanner. The technical effect of using the software tool provided herein to selectively eliminate CT scans from a CT scan sequence is a subset of CT scans of the CT scan sequence that most advantageously uses an allocated amount of time for executing the CT scan sequence may be determined.

The disclosure also provides support for a method for an imaging system, the method comprising: receiving a scan sequence protocol for a sequence of scans to be performed using the imaging system, modifying the scan sequence protocol to include a delay between each scan and a subsequent scan of the scan sequence to reduce a temperature of one or more components of an X-ray tube of the imaging system to a target temperature for performing the subsequent scan, where the delay has a duration that is customized based on the scan and the subsequent scan, and executing the modified scan sequence using the imaging system. In a first example of the method, the scan sequence protocol is an image quality (IQ) test protocol for a sequence of scans to be performed as part of an IQ calibration procedure of the imaging system. In a second example of the method, optionally including the first example, a first duration of the modified scan sequence is less than a second duration of the scan sequence. In a third example of the method, optionally including one or both of the first and second examples, modifying the scan sequence protocol to include the delay between each scan and the subsequent scan of the scan sequence further comprises: for each scan of the scan sequence protocol: parsing a first scan protocol of the scan to extract a first set of scanning parameters of the scan, parsing a second scan protocol of the subsequent scan to extract a second set of scanning parameters of the subsequent scan, estimating thermal limits of a plurality of components of an X-ray tube of the imaging system, based on the first set of scanning parameters and the second set of scanning parameters, calculating a minimum delay for cooling the plurality of components after the scan and prior to performing the subsequent scan, based on the calculated thermal limits, and modifying the scan sequence protocol to include the calculated delay. In a fourth example of the method, optionally including one or more or each of the first through third examples, estimating the thermal limits of the plurality of components of the X-ray tube based on the first set of scanning parameters and the second set of scanning parameters further comprises estimating a thermal limit of each component of the plurality of components using a physics-based model, the physics-based model taking as inputs the first set of scanning parameters and the second set of scanning parameters. In a fifth example of the method, optionally including one or more or each of the first through fourth examples, the physics-based model is used to determine predicted initial temperatures and/or desired baseline temperatures of various components of the X-ray tube prior to performing the scan. In a sixth example of the method, optionally including one or more or each of the first through fifth examples, calculating the minimum delay for cooling the plurality of components after the scan and prior to performing the subsequent scan further comprises: for each component of the plurality of components, calculating a minimum delay for cooling the component based on the calculated thermal limits and the predicted initial temperatures and/or desired baseline temperatures of the various components for the subsequent scan, and selecting a longest delay of the minimum delays of each of the components as the minimum delay for cooling the plurality of components. In a seventh example of the method, optionally including one or more or each of the first through sixth examples, modifying the scan sequence protocol to include the delay between each scan and the subsequent scan of the scan sequence further comprises adjusting a delay of a standard duration between each scan and the subsequent scan to the delay customized to the scan and the subsequent scan, the customized delay having a duration that is shorter than the standard duration. In a eighth example of the method, optionally including one or more or each of the first through seventh examples, the method further comprises: receiving a time constraint for performing the scan sequence, the time constraint an amount of time allocated for performing the scan sequence, determining that a total amount of time of the scan sequence is greater than the time constraint, and in response, modifying the scan sequence protocol to include the customized delay between each scan and the subsequent scan of the scan sequence. In a ninth example of the method, optionally including one or more or each of the first through eighth examples, the method further comprises: determining that the total amount of time of the modified scan sequence is greater than the time constraint, and in response, further modifying the scan sequence protocol to remove one or more scans from the modified scan sequence protocol. In a tenth example of the method, optionally including one or more or each of the first through ninth examples, modifying the scan sequence protocol to remove the one or more scans from the modified scan sequence protocol further comprises: displaying a list of scans of the modified scan sequence protocol within a graphical user interface (GUI), receiving a user input of a selection of scans to be removed from the modified scan sequence protocol, and generating a second modified scan sequence protocol not including the received selection of scans to be removed. In a eleventh example of the method, optionally including one or more or each of the first through tenth examples, modifying the scan sequence protocol to remove the one or more scans from the modified scan sequence protocol further comprises: receiving a user input of a selection of a scanning parameter of the modified scan sequence protocol, ordering the scans of the modified scan sequence protocol in a descending order based on a magnitude of the scanning parameter, sequentially eliminating scans of the modified scan sequence protocol in the descending order until a total duration of the modified scan sequence is less than the time constraint. In a twelfth example of the method, optionally including one or more or each of the first through eleventh examples, modifying the scan sequence protocol to remove the one or more scans from the modified scan sequence protocol further comprises: performing a brute force calculation of a total amount of time of plurality of combinations of scans of the modified scan sequence protocol to determine a combination of scans that maximizes a number of scans included in the modified scan sequence protocol, while maintaining the total amount of time less than the time constraint.

The disclosure also provides support for a scan sequence protocol optimizer software tool, comprising: a physics-based model of an X-ray tube of an imaging system, a processor, and a memory storing instructions that when executed, cause the processor to: receive a scan sequence protocol for a sequence of scans to be performed on the imaging system, perform a first modification of the scan sequence protocol to include a delay between each scan and a subsequent scan of the scan sequence to reduce a temperature of components of an X-ray tube of the imaging system to a target temperature for performing the subsequent scan, where the delay has a duration that is determined based on parameters of each of the scan and the subsequent scan, and store the first modified scan sequence protocol in the memory and/or export the first modified scan sequence protocol to the imaging system for performing a sequence of scans in accordance with the first modified scan sequence protocol. In a first example of the system, further instructions are stored in the memory that when executed, cause the processor to: for each scan of the scan sequence protocol: parse a first scan protocol of the scan to extract a first set of scanning parameters of the scan, parse a second scan protocol of the subsequent scan to extract a second set of scanning parameters of the subsequent scan, estimate a thermal limit of a component of an X-ray tube of the imaging system using a physics-based model, based on the first set of scanning parameters and the second set of scanning parameters, calculate a minimum delay for cooling the component after the scan and prior to performing the subsequent scan, based on the calculated thermal limit and a predicted initial temperature and/or desired baseline temperature of the subsequent scan, and generate the first modified scan sequence protocol including the calculated delay. In a second example of the system, optionally including the first example, further instructions are stored in the memory that when executed, cause the processor to: receive a time constraint for executing the first modified scan sequence protocol, the time constraint an amount of time allocated for executing the first modified scan sequence, determine that a total amount of time of the first modified scan sequence is greater than the time constraint, and in response: display a list of scans of the first modified scan sequence protocol within a graphical user interface (GUI) of the scan sequence protocol optimizer software tool, receive a user input via the GUI, in response to the user input, generate a second modified scan sequence protocol including a smaller number of scans than the first modified scan sequence protocol, and store the second modified scan sequence protocol in the memory and/or export the second modified scan sequence protocol to the imaging system for performing a sequence of scans in accordance with the second modified scan sequence protocol. In a third example of the system, optionally including one or both of the first and second examples, further instructions are stored in the memory that when executed, cause the processor to perform one of: in response to the user input including one or more scans of the first modified scan sequence protocol to be removed, remove the one or more scans from the second modified scan sequence, in response to the user input including a selected scanning parameter of the modified scan sequence protocol: order the scans of the first modified scan sequence protocol in a descending order based on a magnitude of the scanning parameter, and sequentially remove scans of the first modified scan sequence protocol in the descending order until a total duration of the second modified scan sequence is less than the time constraint, and in response to the user input including a user selection to perform an automatic optimization of the first modified scan sequence: performing a brute force calculation of a total amount of time of plurality of combinations of scans of the first modified scan sequence protocol to determine a combination of scans that maximizes a number of scans included in the second modified scan sequence protocol, while maintaining the total amount of time less than the time constraint. In a fourth example of the system, optionally including one or more or each of the first through third examples, the GUI displays: a first control element for selecting a scan sequence protocol from a list of available scan sequence protocols, a second control element for loading a custom scan sequence protocol from a list of available scan sequence protocols, the custom scan sequence protocol including delays between each scan of the scan sequence protocol of a duration customized to the scan, a third control element for performing an optimization of a selected scan sequence protocol, the optimization adding custom delays between scans of the selected scan sequence protocol, a fourth control element, for storing an optimized scan sequence protocol, a plurality of rows of scanning parameters corresponding to individual scans of the selected scan sequence protocol, the scanning parameters configured to be edited by a user of the scan sequence protocol optimizer software tool, a progress bar indicating a progress of an optimization of the selected scan sequence protocol, a time constraint field configured to receive a time constraint for performing the selected scan sequence protocol, and a simulation of an image reconstructed from a scan of the selected scan sequence protocol. In a fifth example of the system, optionally including one or more or each of the first through fourth examples, the scan sequence protocol optimizer software tool is installed and operated on at least one of: a first computing device of the imaging system, a second computing device of a user of the scan sequence protocol optimizer software tool.

The disclosure also provides support for a method, comprising: determining that an estimated amount of time for performing a scan sequence using an imaging system is greater than an amount of time allocated for performing the scan sequence, and in response: displaying a list of scans included in a protocol of the scan sequence within a graphical user interface (GUI), in a first condition, in response to receiving a selection of scans to be removed from the scan sequence protocol, generating a second scan sequence protocol not including the selection of scans to be removed, in a second condition, in response to receiving a scanning parameter of the scan sequence protocol, ordering the list of scans in a descending order based on a magnitude of the scanning parameter, and sequentially eliminating scans of the scan sequence protocol in the descending order until the estimated amount of time for performing of the second scan sequence is less than the amount of time allocated for performing the scan sequence, in a third condition, in response to not receiving the selection of scans to be removed from the scan sequence protocol and not receiving the scanning parameter of the scan sequence protocol, calculating a total amount of time of each of plurality of combinations of scans of the scan sequence protocol to determine a combination of scans that maximizes a number of scans included in the scan sequence protocol, while maintaining the total amount of time less than the amount of time allocated for performing the scan sequence, and generating a second scan sequence including the combination of scans, and performing the second scan sequence using the imaging system, within the allocated amount of time.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for an imaging system, the method comprising:

receiving a scan sequence protocol for a sequence of scans to be performed using the imaging system;

modifying the scan sequence protocol to include a delay between each scan and a subsequent scan of the scan sequence to reduce a temperature of one or more components of an X-ray tube of the imaging system to a target temperature for performing the subsequent scan, where the delay has a duration that is customized based on the scan and the subsequent scan; and executing the modified scan sequence using the imaging system;

wherein modifying the scan sequence protocol to include the delay between each scan and the subsequent scan of the scan sequence further comprises:

for each scan of the scan sequence protocol:

parsing a first scan protocol of the scan to extract a first set of scanning parameters of the scan;

parsing a second scan protocol of the subsequent scan to extract a second set of scanning parameters of the subsequent scan;

estimating thermal limits of a plurality of components of an X-ray tube of the imaging system, based on the first set of scanning parameters and the second set of scanning parameters;

calculating a minimum delay for cooling the plurality of components after the scan and prior to performing the subsequent scan, based on the calculated thermal limits; and modifying the scan sequence protocol to include the calculated delay.

2. The method of claim 1, wherein the scan sequence protocol is an image quality (IQ) test protocol for a sequence of scans to be performed as part of an IQ calibration procedure of the imaging system.

3. The method of claim 1, wherein a first overall duration of the modified sequence of scans is shorter than a second overall duration of the sequence of scans prior to performing the modification.

4. The method of claim 1, wherein estimating the thermal limits of the plurality of components of the X-ray tube based on the first set of scanning parameters and the second set of scanning parameters further comprises estimating a thermal limit of each component of the plurality of components using a physics-based model, the physics-based model taking as inputs the first set of scanning parameters and the second set of scanning parameters.

5. The method of claim 4, wherein the physics-based model is used to determine predicted initial temperatures and/or desired baseline temperatures of various components of the X-ray tube prior to performing the scan.

6. The method of claim 5, wherein calculating the minimum delay for cooling the plurality of components after the scan and prior to performing the subsequent scan further comprises:

for each component of the plurality of components, calculating a minimum delay for cooling the component based on the calculated thermal limits and the predicted initial temperatures and/or desired baseline temperatures of the various components for the subsequent scan; and selecting a longest delay of the minimum delays of each of the components as the minimum delay for cooling the plurality of components.

7. The method of claim 1, wherein modifying the scan sequence protocol to include the delay between each scan and the subsequent scan of the scan sequence further comprises adjusting a delay of a standard duration between each scan and the subsequent scan to the delay customized to the scan and the subsequent scan, the customized delay having a duration that is shorter than the standard duration.

8. The method of claim 1, further comprising:

receiving a time constraint for performing the scan sequence, where the time constraint is an amount of time allocated for performing the scan sequence;

determining that a total amount of time of the scan sequence is greater than the time constraint, and in response, modifying the scan sequence protocol to include the customized delay between each scan and the subsequent scan of the scan sequence.

9. The method of claim 8, further comprising:

determining that the total amount of time of the modified scan sequence is greater than the time constraint, and in response, further modifying the scan sequence protocol to remove one or more scans from the modified scan sequence protocol.

10. The method of claim 9, wherein modifying the scan sequence protocol to remove the one or more scans from the modified scan sequence protocol further comprises:

displaying a list of scans of the modified scan sequence protocol within a graphical user interface (GUI);

receiving a user input of a selection of scans to be removed from the modified scan sequence protocol; and generating a second modified scan sequence protocol not including the received selection of scans to be removed.

11. The method of claim 9, wherein modifying the scan sequence protocol to remove the one or more scans from the modified scan sequence protocol further comprises:

receiving a user input of a selection of a scanning parameter of the modified scan sequence protocol;

ordering the scans of the modified scan sequence protocol in a descending order based on a magnitude of the scanning parameter;

sequentially eliminating scans of the modified scan sequence protocol in the descending order until a total duration of the modified scan sequence is less than the time constraint.

12. The method of claim 9, wherein modifying the scan sequence protocol to remove the one or more scans from the modified scan sequence protocol further comprises:

performing a brute force calculation of a total amount of time of plurality of combinations of scans of the modified scan sequence protocol to determine a combination of scans that maximizes a number of scans included in the modified scan sequence protocol, while maintaining the total amount of time less than the time constraint.

13. A scan sequence protocol optimizer software tool, comprising:

a physics-based model of an X-ray tube of an imaging system;

a processor, and a memory storing instructions that when executed, cause the processor to:

receive a scan sequence protocol for a sequence of scans to be performed on the imaging system;

perform a first modification of the scan sequence protocol to include a delay between each scan and a subsequent scan of the scan sequence to reduce a temperature of components of an X-ray tube of the imaging system to a target temperature for performing the subsequent scan, where the delay has a duration that is determined based on parameters of each of the scan and the subsequent scan; and store the first modified scan sequence protocol in the memory and/or export the first modified scan sequence protocol to the imaging system for performing a sequence of scans in accordance with the first modified scan sequence protocol.

14. The scan sequence protocol optimizer software tool of claim 13, wherein further instructions are stored in the memory that when executed, cause the processor to:

for each scan of the scan sequence protocol:

parse a first scan protocol of the scan to extract a first set of scanning parameters of the scan;

parse a second scan protocol of the subsequent scan to extract a second set of scanning parameters of the subsequent scan;

estimate a thermal limit of a component of an X-ray tube of the imaging system using a physics-based model, based on the first set of scanning parameters and the second set of scanning parameters;

calculate a minimum delay for cooling the component after the scan and prior to performing the subsequent scan, based on the calculated thermal limit and a predicted initial temperature and/or desired baseline temperature of the subsequent scan; and generate the first modified scan sequence protocol including the calculated delay.

15. The scan sequence protocol optimizer software tool of claim 13, wherein further instructions are stored in the memory that when executed, cause the processor to:

receive a time constraint for executing the first modified scan sequence protocol, the time constraint an amount of time allocated for executing the first modified scan sequence;

determine that a total amount of time of the first modified scan sequence is greater than the time constraint, and in response:

display a list of scans of the first modified scan sequence protocol within a graphical user interface (GUI) of the scan sequence protocol optimizer software tool;

receive a user input via the GUI;

in response to the user input, generate a second modified scan sequence protocol including a smaller number of scans than the first modified scan sequence protocol; and store the second modified scan sequence protocol in the memory and/or export the second modified scan sequence protocol to the imaging system for performing a sequence of scans in accordance with the second modified scan sequence protocol.

16. The scan sequence protocol optimizer software tool of claim 15, wherein further instructions are stored in the memory that when executed, cause the processor to perform one of:

in response to the user input including one or more scans of the first modified scan sequence protocol to be removed, remove the one or more scans from the second modified scan sequence;

in response to the user input including a selected scanning parameter of the modified scan sequence protocol:

order the scans of the first modified scan sequence protocol in a descending order based on a magnitude of the scanning parameter; and sequentially remove scans of the first modified scan sequence protocol in the descending order until a total duration of the second modified scan sequence is less than the time constraint; and in response to the user input including a user selection to perform an automatic optimization of the first modified scan sequence:

performing a brute force calculation of a total amount of time of plurality of combinations of scans of the first modified scan sequence protocol to determine a combination of scans that maximizes a number of scans included in the second modified scan sequence protocol, while maintaining the total amount of time less than the time constraint.

17. The scan sequence protocol optimizer software tool of claim 13, wherein the GUI displays:

a first control element for selecting a scan sequence protocol from a list of available scan sequence protocols;

a second control element for loading a custom scan sequence protocol from a list of available scan sequence protocols, the custom scan sequence protocol including delays between each scan of the scan sequence protocol of a duration customized to the scan;

a third control element for performing an optimization of a selected scan sequence protocol, the optimization adding custom delays between scans of the selected scan sequence protocol;

a fourth control element, for storing an optimized scan sequence protocol;

a plurality of rows of scanning parameters corresponding to individual scans of the selected scan sequence protocol, the scanning parameters configured to be edited by a user of the scan sequence protocol optimizer software tool;

a progress bar indicating a progress of an optimization of the selected scan sequence protocol;

a time constraint field configured to receive a time constraint for performing the selected scan sequence protocol; and a simulation of an image reconstructed from a scan of the selected scan sequence protocol.

18. The scan sequence protocol optimizer software tool of claim 13, wherein the scan sequence protocol optimizer software tool is installed and operated on at least one of:

a first computing device of the imaging system;

a second computing device of a user of the scan sequence protocol optimizer software tool.

19. A method, comprising:

determining that an estimated amount of time for performing a scan sequence using an imaging system is greater than an amount of time allocated for performing the scan sequence, and in response:

displaying a list of scans included in a protocol of the scan sequence within a graphical user interface (GUI);

in a first condition, in response to receiving a selection of scans to be removed from the scan sequence protocol, generating a second scan sequence protocol not including the selection of scans to be removed;

in a second condition, in response to receiving a scanning parameter of the scan sequence protocol, ordering the list of scans in a descending order based on a magnitude of the scanning parameter, and sequentially eliminating scans of the scan sequence protocol in the descending order until the estimated amount of time for performing of the second scan sequence is less than the amount of time allocated for performing the scan sequence;

in a third condition, in response to not receiving the selection of scans to be removed from the scan sequence protocol and not receiving the scanning parameter of the scan sequence protocol, calculating a total amount of time of each of plurality of combinations of scans of the scan sequence protocol to determine a combination of scans that maximizes a number of scans included in the scan sequence protocol, while maintaining the total amount of time less than the amount of time allocated for performing the scan sequence, and generating a second scan sequence including the combination of scans; and performing the second scan sequence using the imaging system, within the allocated amount of time.

* * * * *